(12) United States Patent
Itabasi et al.

(10) Patent No.: US 10,847,561 B2
(45) Date of Patent: Nov. 24, 2020

(54) SOLID-STATE IMAGING ELEMENT AND METHOD FOR MANUFACTURING THE SAME, AND ELECTRONIC DEVICE

(71) Applicant: SONY SEMICONDUCTOR SOLUTIONS CORPORATION, Kanagawa (JP)

(72) Inventors: Kouichi Itabasi, Kumamoto (JP); Yuuji Nishimura, Kumamoto (JP); Mitsuru Ishikawa, Kumamoto (JP); Yuichi Seki, Kumamoto (JP); Masaya Shimoji, Kumamoto (JP)

(73) Assignee: Sony Semiconductor Solutions Corporation, Kanagawa (JP)

( * ) Notice: Subject to any disclaimer, the term of this patent is extended or adjusted under 35 U.S.C. 154(b) by 0 days.

(21) Appl. No.: 16/336,009

(22) PCT Filed: Sep. 28, 2017

(86) PCT No.: PCT/JP2017/035190
§ 371 (c)(1),
(2) Date: Mar. 22, 2019

(87) PCT Pub. No.: WO2018/070259
PCT Pub. Date: Apr. 19, 2018

(65) Prior Publication Data
US 2020/0185443 A1    Jun. 11, 2020

(30) Foreign Application Priority Data
Oct. 12, 2016  (JP) .................. 2016-200642

(51) Int. Cl.
*H01L 27/146*      (2006.01)

(52) U.S. Cl.
CPC .... *H01L 27/14627* (2013.01); *H01L 27/1462* (2013.01); *H01L 27/14621* (2013.01); *H01L 27/14685* (2013.01)

(58) Field of Classification Search
CPC ......... H01L 27/14627; H01L 27/14685; H01L 27/1462; H01L 27/14643; H01L 27/14645; H01L 31/02162
See application file for complete search history.

(56) References Cited

U.S. PATENT DOCUMENTS

2009/0039454 A1    2/2009  Masuda et al.
2012/0086039 A1*   4/2012  Won ..................... H01L 33/505
                                                        257/98
(Continued)

FOREIGN PATENT DOCUMENTS

CN    101364607 A    2/2009
CN    102446937 A    5/2012
(Continued)

OTHER PUBLICATIONS

International Search Report and Written Opinion of PCT Application No. PCT/JP2017/035190, dated Dec. 26, 2017, 09 pages of ISRWO.

*Primary Examiner* — Hsien Ming Lee
(74) *Attorney, Agent, or Firm* — Chip Law Group

(57) ABSTRACT

The present technology relates to a solid-state imaging element that is capable of suppressing occurrence of flares, ghosts, and color-mixing, and is capable of suppressing occurrence of stains caused by moisture and a method for manufacturing the same, and an electronic device. The solid-state imaging element includes a pixel in which a single-layered anti-reflective film is formed on a surface of a microlens and a pixel in which a double-layered anti-reflective film is formed on the surface of the microlens. For (Continued)

example, the present technology is applicable to a rear surface irradiation-type solid-state imaging element.

11 Claims, 21 Drawing Sheets

(56) References Cited

U.S. PATENT DOCUMENTS

| | | | |
|---|---|---|---|
| 2012/0086093 A1 | 4/2012 | Otsuka et al. | |
| 2014/0111392 A1* | 4/2014 | Ou | H01P 5/08 343/767 |
| 2015/0228689 A1* | 8/2015 | Lenchenkov | H01L 27/14649 257/432 |
| 2015/0325612 A1* | 11/2015 | Tu | H01L 27/14629 257/432 |
| 2017/0278889 A1 | 9/2017 | Nakashikiryo et al. | |

FOREIGN PATENT DOCUMENTS

| | | |
|---|---|---|
| CN | 107078137 A | 8/2017 |
| JP | 2007-019435 A | 1/2007 |
| JP | 2009-043772 A | 2/2009 |
| JP | 2012-084608 A | 4/2012 |
| KR | 10-2012-0052856 A | 5/2012 |
| TW | 201222798 A | 6/2012 |
| WO | 2016/052220 A1 | 4/2016 |

\* cited by examiner

SOLID-STATE IMAGING ELEMENT AND METHOD FOR MANUFACTURING THE SAME, AND ELECTRONIC DEVICE

CROSS REFERENCE TO RELATED APPLICATIONS

This application is a U.S. National Phase of International Patent Application No. PCT/JP2017/035190 filed on Sep. 28, 2017, which claims priority benefit of Japanese Patent Application No. JP 2016-200642 filed in the Japan Patent Office on Oct. 12, 2016. Each of the above-referenced applications is hereby incorporated herein by reference in its entirety.

TECHNICAL FIELD

The present technology relates to a solid-state imaging element and a method for manufacturing the same, and an electronic device, and particularly, to a solid-state imaging element capable of suppressing image quality deterioration that is caused by moisture between a microlens and an anti-reflective film and a method for manufacturing the same, and an electronic device.

BACKGROUND ART

Currently, a rear surface irradiation-type solid-state imaging element has been spreading. The rear surface irradiation-type solid-state imaging element is more advantageous in comparison to a front surface irradiation-type solid-state imaging element from the viewpoints of miniaturization of a pixel, high sensitivity, an improvement of shading characteristics, and the like.

However, in the rear surface irradiation-type solid-state imaging element, a metal wiring layer is not formed in a route until incident light is received by a photodiode (PD), and thus reflected light is further received by the PD on a microlens surface and the like in comparison to the front surface irradiation-type solid-state imaging element in which the metal wiring layer is formed. Accordingly, in the rear surface irradiation-type solid-state imaging element, flares, ghosts, and color-mixing are more likely to occur in comparison to the front surface irradiation-type solid-state imaging element, and the occurrence becomes a main factor that causes imaging quality deterioration of an image that is generated.

Here, for example, Patent Document 1 suggests a configuration of a rear surface irradiation-type solid-state imaging element in which a double-layered anti-reflective film is formed on a surface of a microlens.

In addition, Patent Document 2 suggests a solid-state imaging element in which a microlens is formed in two layers including a first lens layer and a second lens layer, and an anti-reflective film is formed on the second lens layer on an upper side.

CITATION LIST

Patent Document

Patent Document 1: Japanese Patent Application Laid-Open No. 2012-84608
Patent Document 2: Japanese Patent Application Laid-Open No. 2007-19435

SUMMARY OF THE INVENTION

Problems to be Solved by the Invention

When forming an anti-reflective film on a surface of a microlens, if a material having low moisture permeability is used as the anti-reflective film, dehumidification of a microlens material is not sufficient, and thus stains occur.

The present technology has been made in consideration of such circumstances, and an object thereof is to suppress not only reflection from a microlens surface, but also occurrence of stains caused by insufficient dehumidification of a microlens material.

Solutions to Problems

According to a first aspect of the present technology, there is provided a solid-state imaging element. Each pixel includes a photoelectric conversion unit that performs photoelectric conversion in correspondence with incident light, and a microlens that condenses the incident light to the photoelectric conversion unit. A pixel in which a multi-layered anti-reflective film is formed on a surface of the microlens and a pixel in which a single-layered anti-reflective film is formed on the surface of the microlens are mixed in.

The pixel in which the single-layered anti-reflective film is formed on the surface of the microlens may be set to a pixel obtained by removing an anti-reflective film having moisture permeability lower than moisture permeability of the single-layered anti-reflective film from the pixel in which the multi-layered anti-reflective film is formed on the surface of the microlens.

Pixels corresponding to one-fourth of the entirety of pixels may be set to pixels in which the single-layered anti-reflective film is formed on the surface of the microlens.

The solid-state imaging element according to the first aspect of the present technology may further include a color filter that is provided between the photoelectric conversion unit and the microlens, and all pixels, in which the color filter has a predetermined color, among the entirety of pixels may be set to pixels in which the single-layered anti-reflective film is formed on the surface of the microlens.

The color filter may be formed in a Bayer array, and all pixels, in which the color filter is set to G, among the entirety of pixels may be set to pixels in which the single-layered anti-reflective film is formed on the surface of the microlens.

The color filter may be formed in a Bayer array, and all pixels, in which the color filter is set to B, among the entirety of pixels may be set to pixels in which the single-layered anti-reflective film is formed on the surface of the microlens.

The multi-layered anti-reflective film may be constituted by a first anti-reflective film and a second anti-reflective film, the single-layered anti-reflective film may be constituted by the second anti-reflective film, the first anti-reflective film may be a silicon nitride film or a silicon oxynitride film, and the second anti-reflective film may be a silicon oxide film or a silicon oxycarbide film.

Refractive indexes of the microlens, the first anti-reflective film, and the second anti-reflective film may satisfy a relationship of the first anti-reflective film> the microlens> the second anti-reflective film.

The solid-state imaging element may be set to a rear surface irradiation type.

According to a second aspect of the present technology, there is provided a method for manufacturing a solid-state imaging element. The method includes: forming a microlens that condenses incident light to a photoelectric conversion unit in each pixel; and forming a multi-layered anti-reflective film on a surface of the microlens in a first pixel, and forming a single-layered anti-reflective film on the surface of the microlens in a second pixel.

According to a third aspect of the present technology, there is provided an electronic device including a solid-state imaging element. Each pixel of the solid-state imaging element includes a photoelectric conversion unit that performs photoelectric conversion in correspondence with incident light, and a microlens that condenses the incident light to the photoelectric conversion unit. A pixel in which a multi-layered anti-reflective film is formed on a surface of the microlens and a pixel in which a single-layered anti-reflective film is formed on the surface of the microlens are mixed in.

In the first to third aspect of the present technology, a pixel in which a multi-layered anti-reflective film is formed on a surface of the microlens and a pixel in which a single-layered anti-reflective film is formed on the surface of the microlens are provided in a solid-state imaging element.

Effects of the Invention

According to the first aspect and the second aspect of the present technology, it is possible to suppress occurrence of flares, ghosts, and color-mixing, and it is possible to suppress occurrence of stains caused by moisture, and deterioration of sensitivity characteristics of pixels

MODE FOR CARRYING OUT THE INVENTION

Hereinafter, best modes for carrying out the present technology (hereinafter, referred to as "embodiment") will be described in detail with reference to the accompanying drawings.

<Prehistory Leading to Present Technology>

First, description will be given of a prehistory that leads to an embodiment of the present technology.

Representative uses of a rear surface irradiation-type solid-state imaging element include a use for a compact digital camera and a use for a mobile camera. The rear surface irradiation-type solid-state imaging element was previously put into practical use with respect to an imaging element including a minute pixel having a unit pixel size of approximately 1.75 um.

The rear surface irradiation-type solid-state imaging element was also applicable to digital cameras having a so-called APS size, 35 mm, 1-type size, and the like, but a pixel size of the imaging elements is sufficiently larger than a pixel size such as approximately 1.75 um, and thus introduction thereof was late.

However, in recent, application of the rear surface irradiation type has been examined with respect to an imaging element having a large pixel size to realize imaging quality with high sensitivity and high definition.

Figure 1:
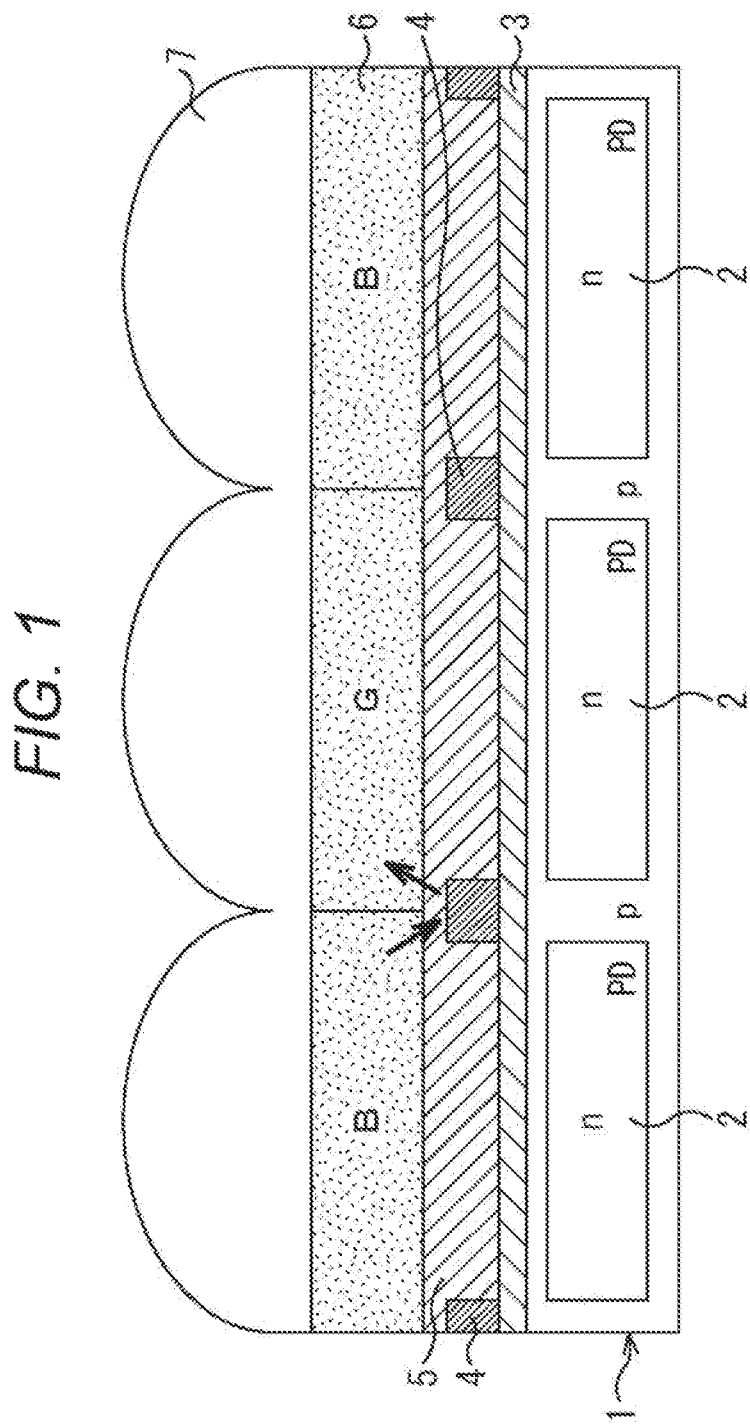
FIG. 1 is a cross-sectional view illustrating a basic pixel structure of a rear surface irradiation-type solid-state imaging element.

FIG. 1 is a cross-sectional view illustrating a basic pixel structure of the rear surface irradiation-type solid-state imaging element.

With respect to a semiconductor substrate 1 as a p-type semiconductor region, an n-type semiconductor region 2 is formed for every pixel. Thus, a pn junction-type photodiode PD is constituted for every pixel. The photodiode PD is a photoelectric conversion unit that performs photoelectric conversion in correspondence with incident light. An upper surface of the semiconductor substrate 1 in FIG. 1 becomes a light incident surface. Although not illustrated in the drawing, a pixel transistor that reads out charges stored in the photodiode PD, and a metal wiring layer including a multi-layered metal wiring and an interlayer insulating film are formed on a lower surface.

An anti-reflective film 3 is formed on the entirety of the upper surface that is the light incident surface of the semiconductor substrate 1. For example, the anti-reflective film 3 is formed in a double-layered structure including a hafnium oxide ($HfO_2$) film and a silicon oxide film.

In addition, a light-shielding film 4 constituted by a metallic material such as aluminum (Al), tungsten (W), and copper (Cu) is formed on an upper surface of the anti-reflective film 3 at a pixel boundary portion, and a color filter 6 is formed on the upper surface of the light-shielding film 4 and the anti-reflective film 3 through a planarization film 5. For example, the color filter 6 is formed in a so-called Bayer array so that four pixels of 2×2 allows light of G, R, B, and G to be transmitted therethrough. A microlens 7 is formed on the color filter 6. The microlens 7 condenses the incident light to be incident to the photodiode PD.

In the rear surface irradiation-type solid-state imaging element configured as described above, a metal wiring layer does not exist on a light incident side, and thus the photodiode PD can efficiently take the incident light. As a result, sensitivity characteristics are excellent. On the other hand, since the metal wiring layer does not exist, there is a concern about optical color-mixing due to light incidence to adjacent pixels. Therefore, the light-shielding film 4 is disposed between pixels to reduce the optical color-mixing.

Figure 2:
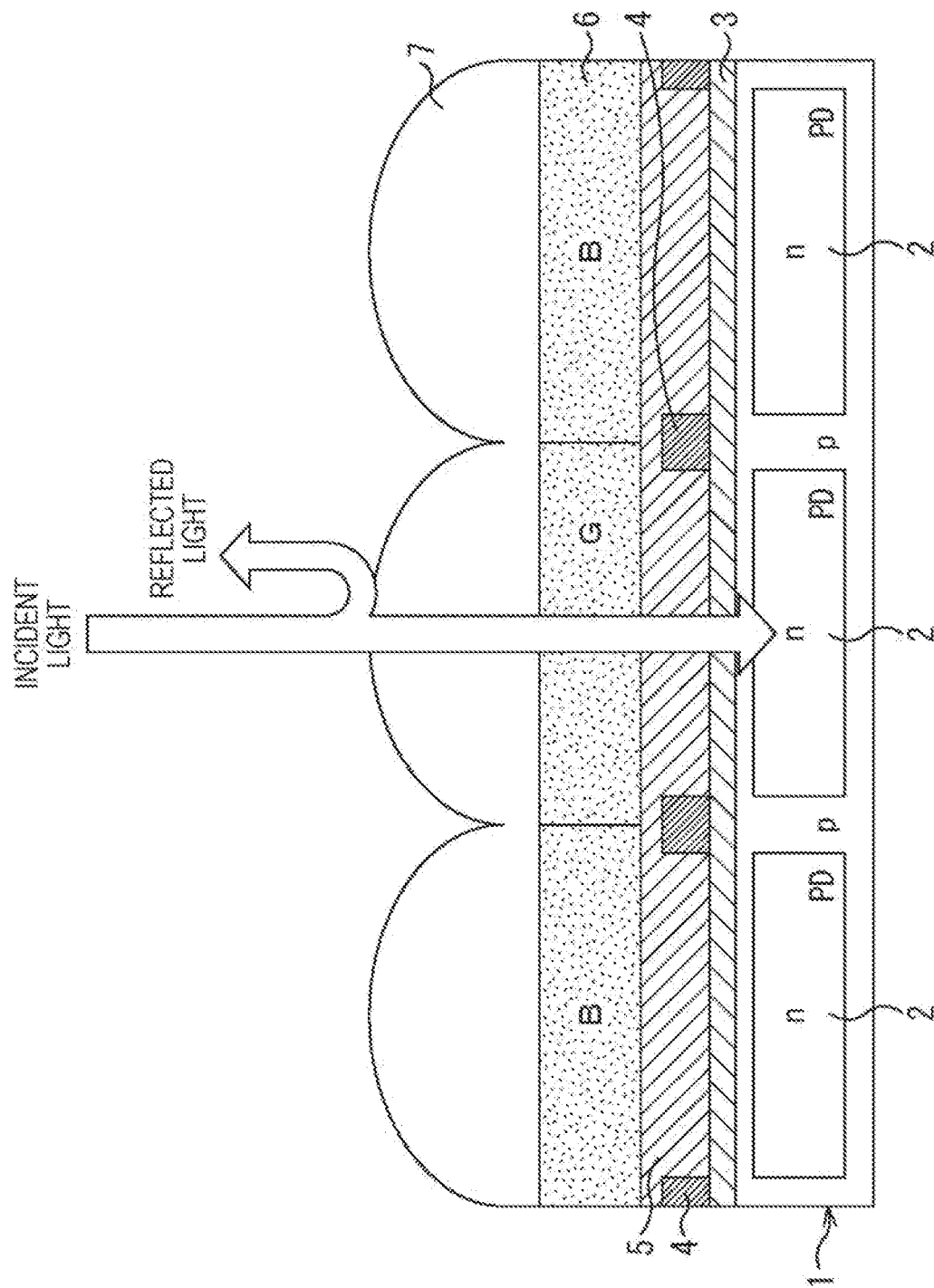
FIG. 2 is a view describing reflection from a surface of a microlens.

However, in addition to light that is incident from adjacent pixels, reflected light from a seal glass surface, reflected light from an infrared cutter filter, reflected light from an optical system of a camera set, and the like are also incident to the photodiode PD, and thus the reflected light and the like become a main factor that causes occurrence of flares, ghosts, and color-mixing. Particularly, as a cause of occurrence of flares, ghosts, and color-mixing component light, as illustrated in FIG. 2, reflection from a surface of the microlens 7 can be exemplified.

As a material of the microlens 7, for example, an acrylic resin, a styrenic resin, a novolac resin, or a co-polymeric resin thereof can be used, and a refractive index thereof is approximately 1.48 to 1.62.

For example, when a medium on an incident light side is assumed as air, surface reflection of the microlens 7 becomes approximately 3.8% to 5.6%. When the refractive index of the microlens 7 is great, the surface reflectivity becomes higher.

Figure 3:
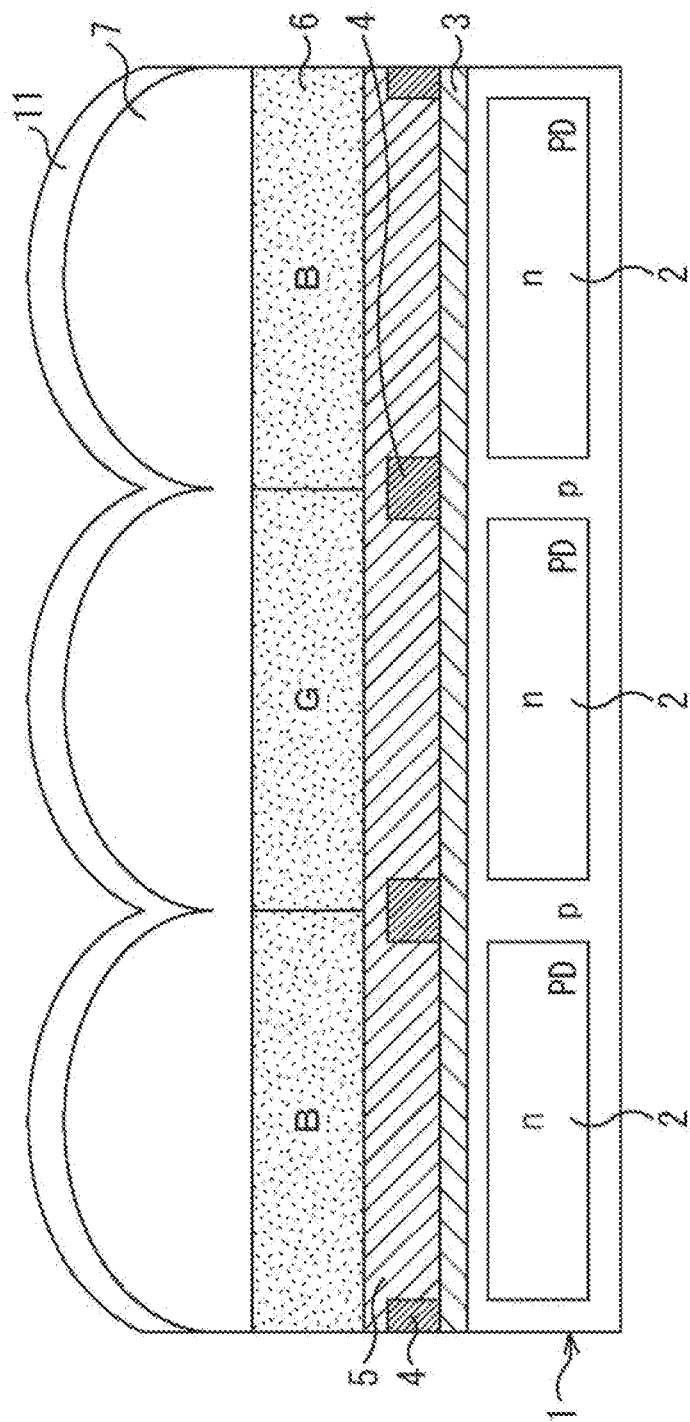
FIG. 3 is a cross-sectional view of the rear surface irradiation-type solid-state imaging element in which a single-layered anti-reflective film is formed on the surface of the microlens.

Here, to prevent reflection from a microlens surface, as illustrated in FIG. 3, an anti-reflective film 11 may be formed on a surface of the microlens 7 to reduce reflectivity.

For example, as a material of the microlens 7, in the case of using a polystyrene-based material having a refractive index of approximately 1.60, with regard to the surface reflectivity, an average reflectivity of visible light (400 to 700 nm) was approximately 5.2%.

As the anti-reflective film 11, when forming a silicon oxide film (SiO) having a refractive index of approximately 1.46 on the surface of the microlens in a single layer at a thickness of approximately 80 nm, the average reflectivity of the microlens 7 was reduced to approximately 2.6%.

However, in the case of a unit pixel that has a unit pixel size such as an APS size, 35 mm, and 1-type size as large as 1.90 um or greater, and can be used in a digital camera (hereinafter, referred to as a large-sized pixel in contrast with the minute pixel) instead of a minute pixel having a unit pixel size of approximately 1.75 um, a sufficient effect is not obtained in a single-layered anti-reflective film 11, and image quality deterioration is caused to occur.

In addition, with regard to light that is incident to the microlens 7, diffracted and reflected light occurs, but a diffraction order m and a diffraction angle θ of the diffracted and reflected light satisfy a relationship of the following Expression (1) with a pitch (pixel size) P of a microlens. In Expression (1), λ represents a wavelength of incident light.

$$P \cdot \sin\theta = m \cdot \lambda \quad (1)$$

As can be seen from Expression (1), when a wavelength λ of incident light is constant, if the pitch P of the microlens decreases, the diffraction order m is reduced. If the pitch P of the microlens increases, the diffraction order m increases. Simultaneously, the smaller the pitch P of the microlens is, the further the diffraction angle θ at the same diffraction order m increases. In addition, the smaller the wavelength λ of the incident light is, the further the diffraction order m increases.

Figure 4:
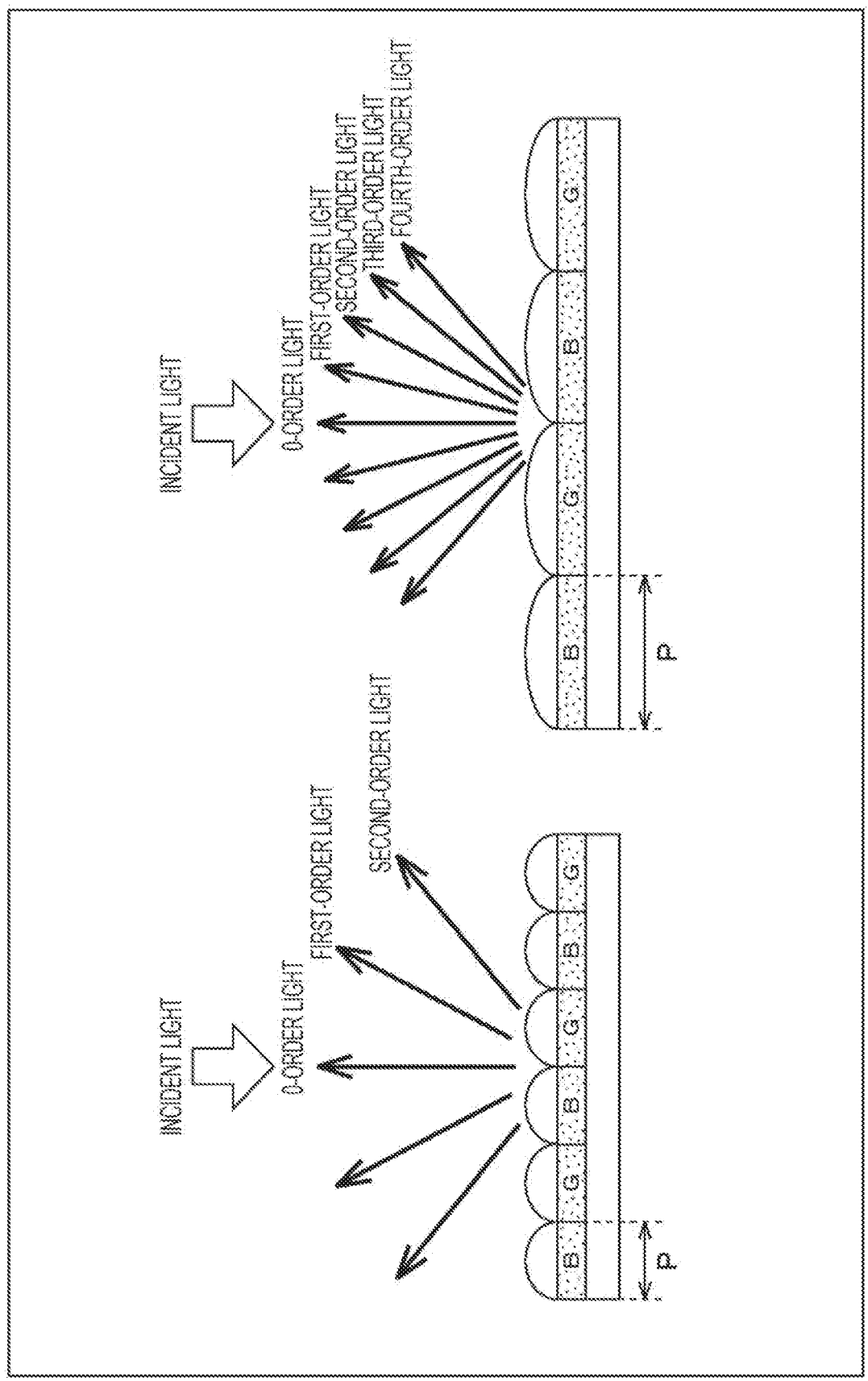
FIG. 4 is a diagram describing a relationship between a unit pixel size and diffracted and reflected light.

Accordingly, as illustrated in FIG. 4, the greater a unit pixel size is, the further the diffraction order m of the diffracted and reflected light increases and the further the diffraction angle θ decreases. Accordingly, the greater the pixel size is, the further an influence of the reflected light increases, and the higher necessity for reduction of the reflected light is.

Here, to further reduce reflected light of a solid-state imaging element including a large-sized pixel, as disclosed in Patent Document 1, a structure in which a double-layered anti-reflective film is formed on a surface of the microlens is considered.

Figure 5:
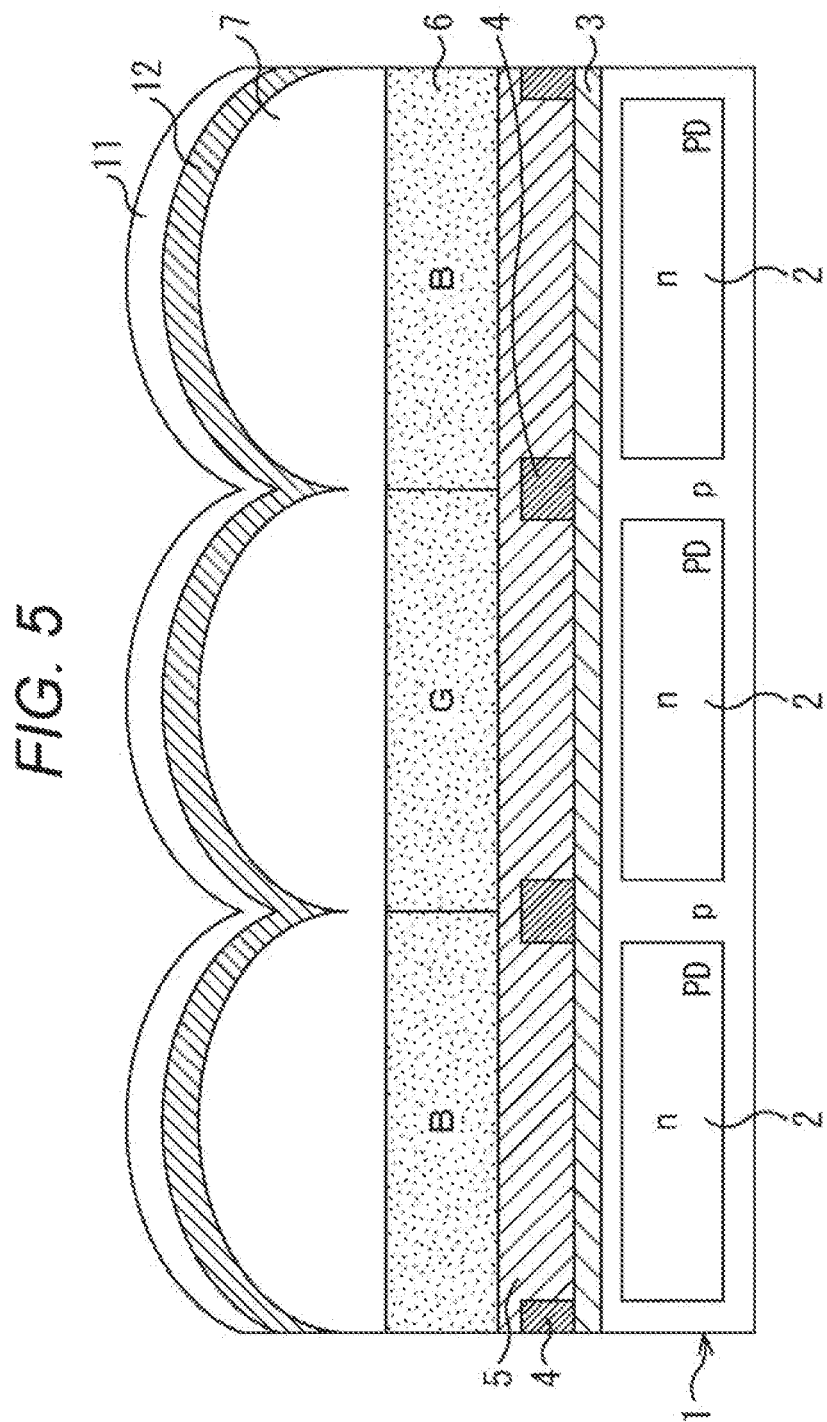
FIG. 5 is a cross-sectional view of the rear surface irradiation-type solid-state imaging element in which a double-layered anti-reflective film is formed on the surface of the microlens.

FIG. 5 is a cross-sectional view of a rear surface irradiation-type solid-state imaging element in which a double-layered anti-reflective film is formed on the surface of the microlens.

In the solid-state imaging element illustrated in FIG. 5, another anti-reflective film 12 is formed between the anti-reflective film 11 formed on the surface of the microlens 7 as illustrated in FIG. 3, and the microlens 7 to obtain a double-layered anti-reflective film. The other structures are similar to those in the solid-state imaging element illustrated in FIG. 3.

Hereinafter, the anti-reflective film 12 that is closer to the microlens 7 is referred to as a first anti-reflective film 12, and the anti-reflective film 11 in an outermost layer is referred to as a second anti-reflective film 11. As in FIG. 3, the second anti-reflective film 11 of an upper layer is formed, for example, in a film thickness of approximately 80 um by using a silicon oxide film (SiO) having a refractive index of approximately 1.46. The first anti-reflective film 12 of a lower layer is formed, for example, in a film thickness of approximately 120 um by using a silicon nitride film (SiN) having a refractive index of approximately 1.86.

In the pixel structure illustrated in FIG. 5 in which the anti-reflective film is set to a double-layered structure, and a unit pixel size is set to 2.4 um for a 1-type size camera use, from a measurement result of the surface reflectivity, the average reflectivity of visible light (400 to 700 nm) was approximately 1.3%. In the pixel structure illustrated in FIG. 3 in which only the above-described single-layered anti-reflective film 11 is provided, the average reflectivity of the microlens 7 is approximately 2.6%, reflectivity of the double-layered structure is the half of the reflectivity of the single-layered structure, and is approximately ¼ times reflectivity in a case where the anti-reflective film is not formed. Accordingly, a satisfactory anti-reflection effect was obtained.

In addition, with respect to the rear surface irradiation-type solid-state imaging element in which the anti-reflective film having a double-layered structure is formed, from an examination result of sensitivity characteristics, an improvement of 2% was exhibited due to a reduction effect of the surface reflectivity of the microlens 7. With regard to flares and ghosts, it is difficult to carry out quantitative evaluation, and thus sensory evaluation was performed under a constant imaging environment. From the sensory evaluation, the rear surface irradiation-type solid-state imaging element in which the anti-reflective film having a double-layered structure is formed was within a permissible level.

However, as a reliability test, a test of storing the rear surface irradiation-type solid-state imaging element in which the anti-reflective film having a double-layered structure is formed for a constant period was performed under a high-temperature and high-humidity environment. Specifically, a test of storing the solid-state imaging element including the double-layered anti-reflective film for 1000 hours was performed under an environment of a temperature of 85° C. and a humidity of 85%. After storage under the environment, in the solid-state imaging element including the double-layered anti-reflective film, as illustrated in FIG. 6, stains which are not exhibited in a solid-state imaging element including a single-layered anti-reflective film were found.

Figure 6:
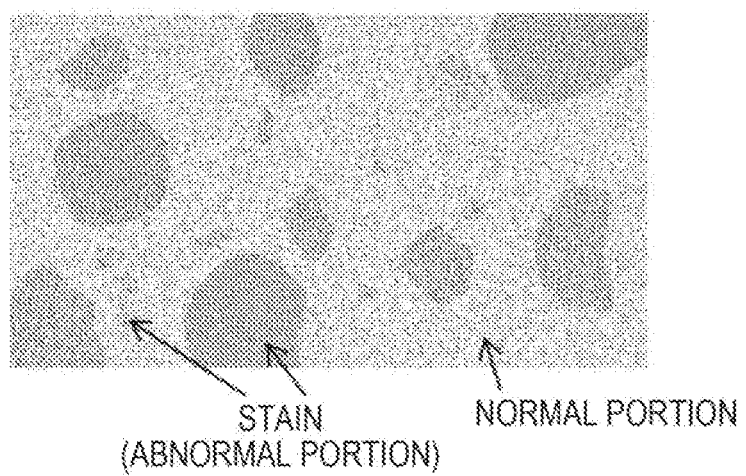
FIG. 6 is a view illustrating an example of stains which occur when forming the double-layered anti-reflective film.
Figure 7:
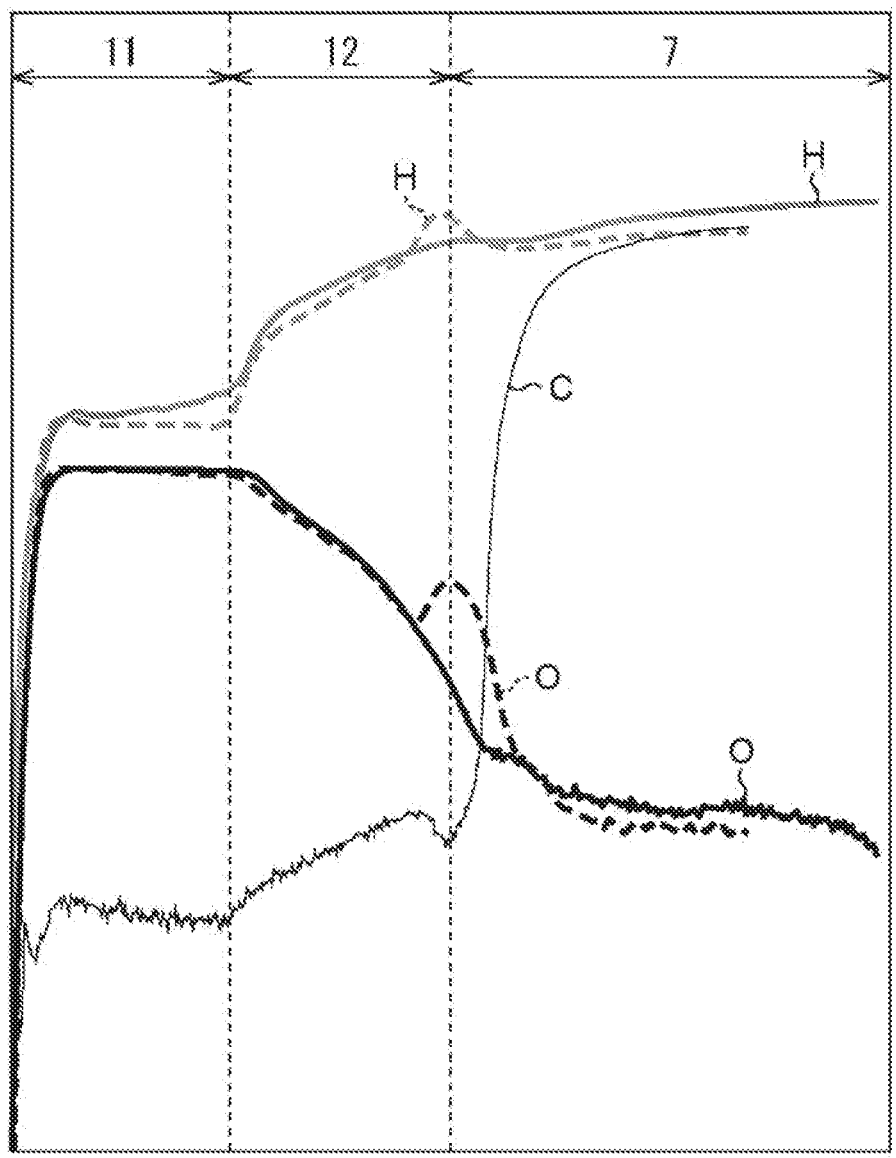
FIG. 7 is a diagram describing a result obtained by analyzing moisture of the double-layered anti-reflective film and the microlens.

From analysis of the second anti-reflective film 11, the first anti-reflective film 12, and a portion of the microlens 7 in a region in which the stains as illustrated in FIG. 6 ion occurred with secondary ion mass spectrometry, a measurement result indicated by a broken line in FIG. 7 was obtained with respect to secondary ions of H and O which relate to moisture.

In the graph in FIG. 7, the horizontal axis represents positions of the second anti-reflective film 11, the first anti-reflective film 12, and the microlens 7 in respective layers, and the vertical axis represents an ion concentration.

In the ion concentration at positions in the respective layers as indicated by a broken line in FIG. 7, an ion concentration of any of H and O rises between the first anti-reflective film 12 and the microlens 7. From the measurement result, it is considered that the silicon nitride film (SiN) used as the first anti-reflective film 12 is a film having low moisture permeability, and thus moisture formed a residue between the first anti-reflective film 12 and the microlens 7, and stains occurred as illustrated in FIG. 6.

Figure 8:
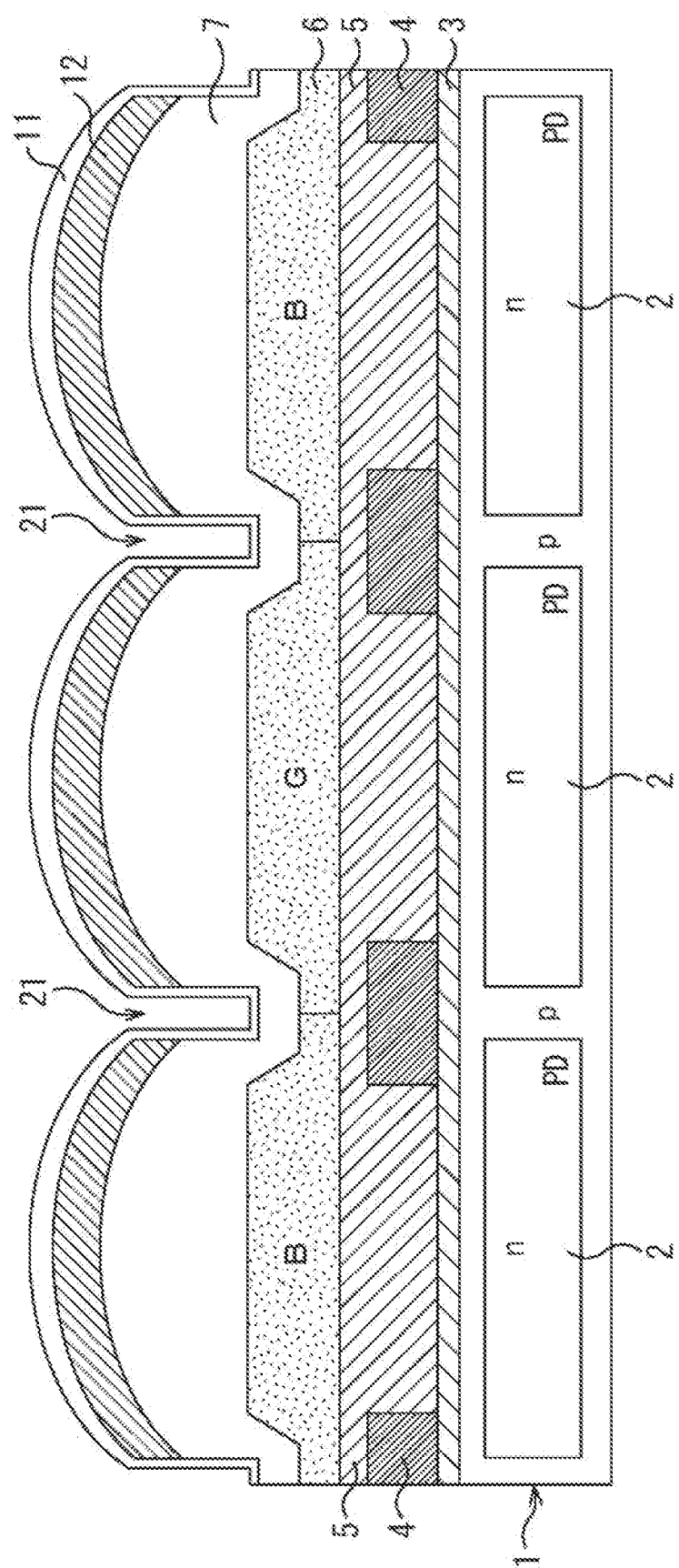
FIG. 8 is a cross-sectional view of a pixel structure in which a trench is formed at a pixel boundary of the double-layered anti-reflective film.

Here, for example, as illustrated in FIG. 8, a pixel structured in which a trench 21 from which the first anti-reflective film 12 is removed is formed at a boundary portion of pixels in a diagonal direction was prepared for a test, and ion concentrations at positions in respective layers were analyzed.

The ion concentrations of H and O in the pixel structure in which the trench 21 is formed at a boundary portion of pixels in a diagonal direction represent measurement results indicated by a solid line in FIG. 7.

As is clear from comparison between the ion concentrations of H and O as indicated by a solid line in FIG. 7 and the ion concentrations of H and O as indicated by a broken line in FIG. 7, a peak does not exist between the first anti-reflective film 12 and the microlens 7, and moisture permeability is improved due to formation of the trench 21. This represents that the trench 21 from which the first anti-reflective film 12 is removed functions as a moisture permeation port, and occurrence of stains caused by moisture can be suppressed. Furthermore, in the pixel structure illustrated in FIG. 8, the second anti-reflective film 11 is formed on the entire surface including a portion of the trench 21, and thus it can be seen that the second anti-reflective film 11 is a film having high moisture permeability.

However, when the trench 21 is formed at a pixel boundary as illustrated in FIG. 8, a gap (step difference) occurs in microlenses 7 adjacent to each other, and thus condensing efficiency of the microlenses 7 is lowered due to the gap, and sensitivity characteristics of pixels also deteriorate.

Here, the present inventors proposed a pixel structure in which occurrence of stains caused by moisture is suppressed, reflected light is reduced, and a gap is not formed in a microlens to prevent deterioration of sensitivity characteristics due to the gap in a rear surface irradiation-type solid-state imaging element including a large-sized pixel in which a unit pixel size is 1.90 um or greater.

Embodiment of Present Technology

Figure 9:
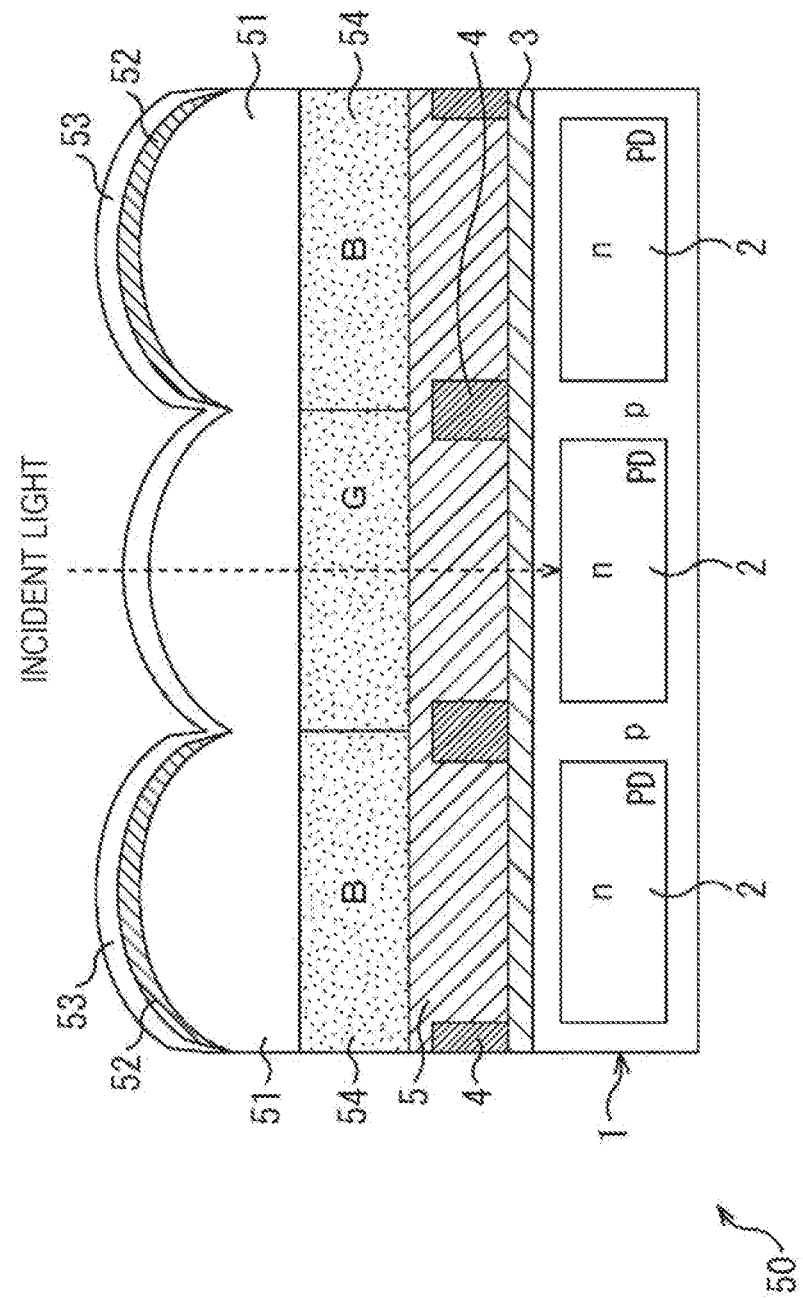
FIG. 9 is cross-sectional view illustrating a configuration example of a rear surface irradiation-type solid-state imaging element to which the present technology is applied.

FIG. 9 is a cross-sectional view illustrating a configuration example of a rear surface irradiation-type solid-state imaging element that is an embodiment of the present technology.

In a rear surface irradiation-type solid-state imaging element 50, only a second anti-reflective film 53 is formed on a surface of a microlens 51 in a specific pixel, and a first anti-reflective film 52 and the second anti-reflective film 53 are formed on the surface of the microlens 51 in the other pixels.

In respective pixels of the rear surface irradiation-type solid-state imaging element 50, a color filter 54 is formed in a lower layer of the microlens 51, and the planarization film 5, the light-shielding film 4, the anti-reflective film 3, and a pn junction-type photodiode PD are formed in lower layers of the color filter 54 as in the configuration illustrated in FIG. 1. Description of a portion in FIG. 9 to which the same reference numeral as in FIG. 1 is given will be omitted.

The microlens 51 is formed by using an acrylic resin, a styrenic resin, a novolac resin, or a co-polymeric resin thereof as a material, and a refractive index thereof is approximately 1.48 to 1.62.

The first anti-reflective film 52 is formed in a film thickness in a range of 90 to 155 nm (for example, 120 nm) by using a material such as SiN and SiON which have a refractive index higher than that of the microlens 51. The refractive index of SiN is approximately 1.81 to 1.90, and the refractive index of SiON is approximately 1.52 to 1.80. The second anti-reflective film 53 is formed in a film thickness in a range of 60 to 100 nm (for example, 80 nm) by using a material such as SiO and SiOC which have a refractive index lower than that of the microlens 51. The refractive index of SiO is approximately 1.47, and the refractive index of SiOC is approximately 1.40. Accordingly, the first anti-reflective film 52 is similar to the first anti-reflective film 12 in FIG. 8, the second anti-reflective film 53 is similar to the second anti-reflective film 11 in FIG. 8, and the first anti-reflective film 52 is a film having moisture permeability lower than that of the second anti-reflective film 53. Refractive indexes of the microlens 51, the first anti-reflective film 52, and the second anti-reflective film 53 satisfy a relationship of the first anti-reflective film 52>the microlens 51>the second anti-reflective film 53.

In a color arrangement of the color filter 54, for example, a Bayer array in which four pixels of 2×2 are repetitively arrayed with an arrangement of G, R, B, and G. However, the color arrangement of the color filter 54 is not limited to the Bayer array, and is arbitrarily selected.

In the example illustrated in FIG. 9, in two pixels of G among four pixels of G, R, B, and G which constitute a repetitive unit in the Bayer array, the first anti-reflective film 52 is not formed on a surface of the microlens 51, and only the second anti-reflective film 53 is formed on the surface. Accordingly, in the two pixels of R and B, a double-layered anti-reflective film including the first anti-reflective film 52 and the second anti-reflective film 53 is formed. In all pixels in a pixel array in which the pixels are two-dimensionally arrayed, all pixels of G become pixels in which a single-layered anti-reflective film (the second anti-reflective film 53 alone) is formed on the surface of the microlens 51.

Figure 10:
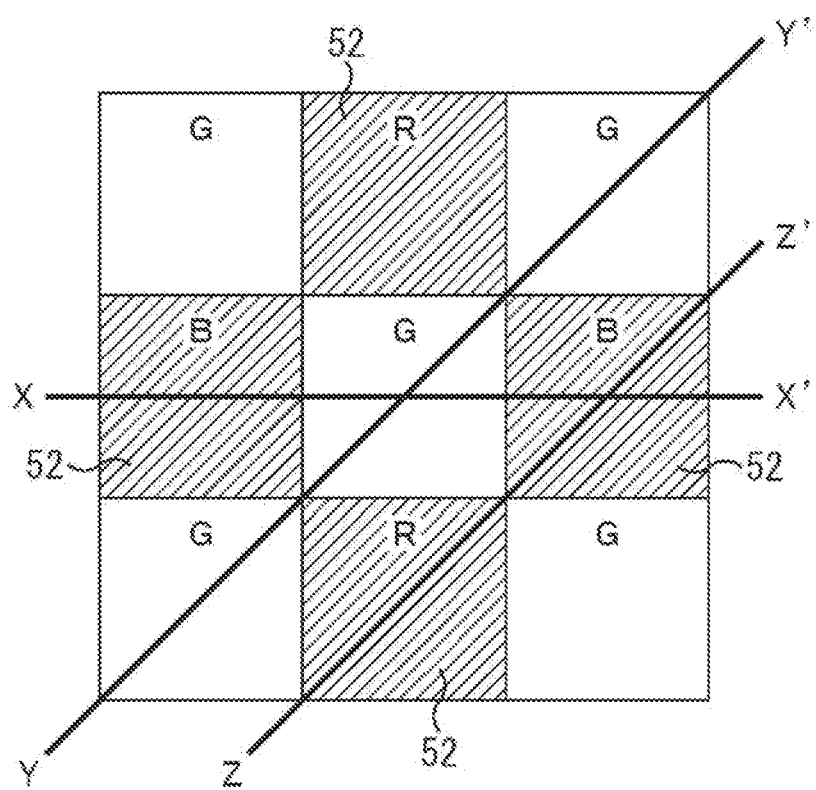
FIG. 10 is a plan view illustrating a pixel arrangement of a first anti-reflective film in FIG. 9.

FIG. 10 is a plan view illustrating a pixel arrangement in which the first anti-reflective film 52 is formed in pixel regions of 3×3. In FIG. 10, a color arrangement of the color filter 54 in respective pixels is indicated by characters of G, R, B, and G.

In FIG. 10, among nine pixels of 3×3 in the Bayer array, the same pattern as in the first anti-reflective film 52 in FIG. 9 is given to a pixel in which the first anti-reflective film 52 is formed. Specifically, the first anti-reflective film 52 is formed in a pixel of R and a pixel of B, but the first anti-reflective film 52 is not formed in a pixel of G. Furthermore, the second anti-reflective film 53 is formed in all pixels, and thus a pixel in which the first anti-reflective film 52 is not formed becomes a pixel in which only the second anti-reflective film 53 is formed.

A cross-sectional view along line segment X-X' in FIG. 10 corresponds to the cross-sectional view in FIG. 9.

Figure 11:
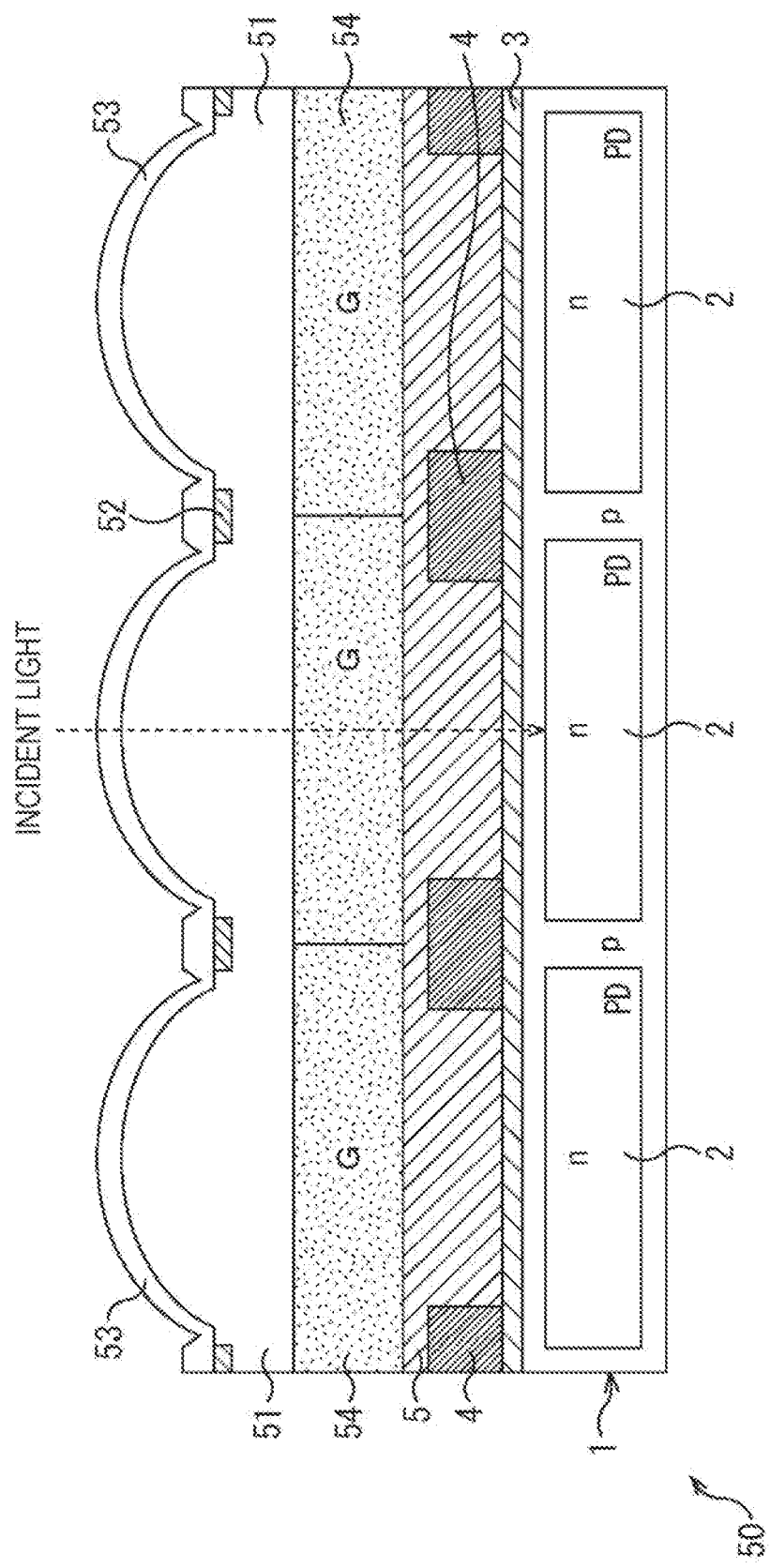
FIG. 11 is a cross-sectional view of the rear surface irradiation-type solid-state imaging element in FIG. 9 which is taken along line segment Y-Y' in FIG. 10.

FIG. 11 is a cross-sectional view taken along line segment Y-Y' in FIG. 10 in a diagonal direction.

All pixels along line segment Y-Y' are pixels of G, and thus the second anti-reflective film 53 is formed, but the first anti-reflective film 52 is formed only at a pixel boundary portion in a diagonal direction, and is not formed in a path of light incident to the photodiode PD.

Figure 12:
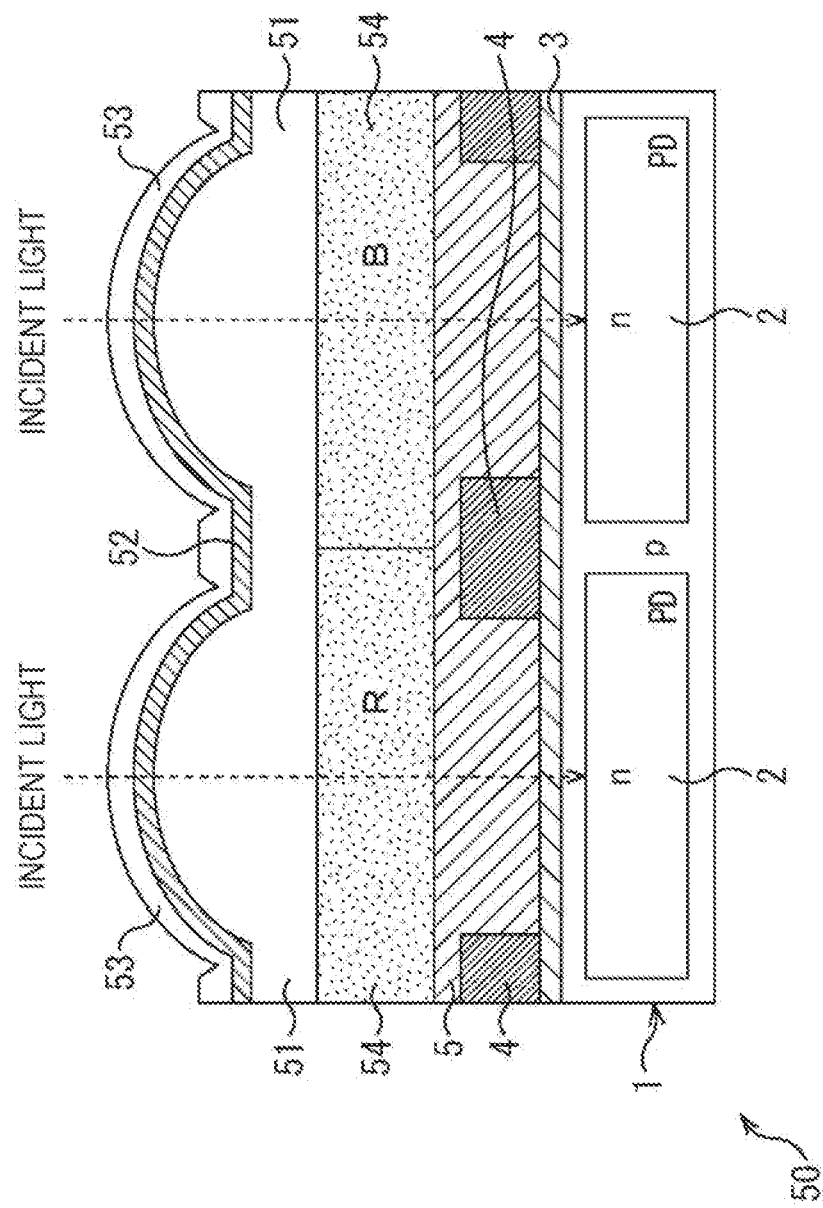
FIG. 12 is a cross-sectional view of the rear surface irradiation-type solid-state imaging element in FIG. 9 which is taken along line segment Z-Z' in FIG. 10.

FIG. 12 is a cross-sectional view along line segment Z-Z' in FIG. 10 in a diagonal direction.

Pixels along line segment Z-Z' are pixels of R or B, and thus a double-layered anti-reflective film including the first anti-reflective film 52 and the second anti-reflective film 53 is formed.

As described above, the rear surface irradiation-type solid-state imaging element 50 includes a pixel in which the single-layered anti-reflective film (the second anti-reflective film 53) is formed on a surface of the microlens 51, and a pixel in which the double-layered anti-reflective film (the first anti-reflective film 52 and the second anti-reflective film 53) is formed.

As described above with reference to the analysis result of FIG. 7, the second anti-reflective film 53 in FIG. 9 which corresponds to the second anti-reflective film 11 in FIG. 8 is a film having high moisture permeability. Accordingly, a pixel in which the first anti-reflective film 52 is not formed and only the second anti-reflective film 53 is formed can release moisture to the outside as in the case of forming the trench 21 in FIG. 8. As a result, it is possible to suppress occurrence of stains caused by moisture.

On the other hand, a pixel in which the double-layered anti-reflective film is formed can sufficiently prevent reflection of incident light from the surface of the microlens 51, and thus it is possible to suppress occurrence of flares, ghosts, and color-mixing.

In addition, in the case of the rear surface irradiation-type solid-state imaging element 50, a height difference of the second anti-reflective film 53 occurs between a pixel of G in which the single-layered anti-reflective film is formed, and pixels of R and B in which the double-layered anti-reflective film is formed due to presence or absence of the first anti-reflective film 52. However, a gap as in the case of forming the trench 21 does not exist, and thus a decrease of condensing efficiency or deterioration of sensitivity characteristics of a pixel does not occur.

In addition, in the case of the rear surface irradiation-type solid-state imaging element 50, a pixel of G in which the single-layered anti-reflective film is formed and pixels of R and B in which the double-layered anti-reflective film is formed are arranged in the Bayer array, and thus a periodicity of a formation pitch P of the microlens 51 becomes two times a pixel pitch. As can be seen from Expression (1), when the periodicity becomes two times, the diffraction order m increases, and intensity of each beam of reflected light becomes weak, and thus it is possible to obtain an effect of dispersing reflection strength.

<Method for Manufacturing Rear Surface Irradiation-Type Solid-State Imaging Element 50>

Next, description will be given of a manufacturing process of the microlens 51, the first anti-reflective film 52, and the second anti-reflective film 53 in the rear surface irradiation-type solid-state imaging element 50.

The microlens 51 constituted by an acrylic resin or the like is formed on an upper surface of the color filter 54, and with respect to the entirety of pixels, the first anti-reflective film 52 is formed on the microlens 51 by using a material having a refractive index higher than that of the microlens 51. Next, in correspondence with a color of the color filter 54, for example, in a case where a pixel of G is set to a single-layered anti-reflective film, only with respect to the pixel of G, the first anti-reflective film 52 is removed. Then, with respect to the entirety of pixels, the second anti-reflective film 53 is formed on the microlens 51 or the first anti-reflective film 52 by using a material having refractive index lower than that of the microlens 51.

Description will be made in more detail with reference to FIGS. 13A 13B 13C, 13D, and 13E.

Figure 13:
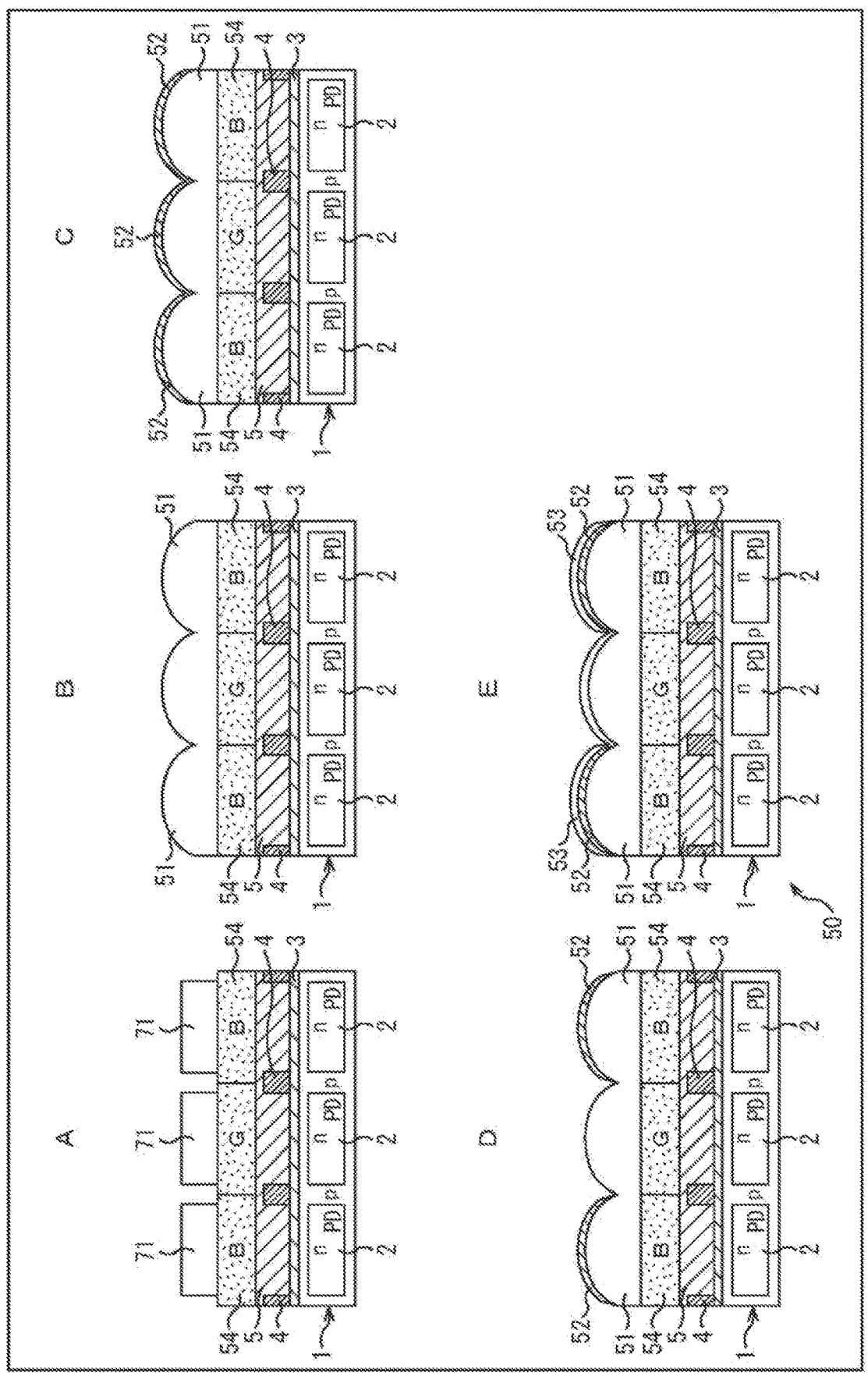
FIGS. 13A, 13B, 13C, 13D, and 13E are views describing a method for manufacturing the rear surface irradiation-type solid-state imaging element in FIG. 9.

As illustrated in FIG. 13A, the anti-reflective film 3, the light-shielding film 4, the planarization film 5, and the color filter 6 are sequentially formed on a light incident side of the semiconductor substrate 1 in which a photodiode PD is formed for every pixel. In addition, for example, a photosensitive resin film 71 is formed on the upper surface of the color filter 6 by using a positive type photosensitive acrylic resin, a positive type photosensitive styrenic resin, a co-polymeric resin thereof, and the like which have a thermal flowability and a thermosetting property, and then the photosensitive resin film 71 is patterned in a pixel unit by a lithography technology.

In addition, as illustrated in FIG. 13B, the photosensitive resin film 71 that is patterned in a pixel unit is deformed into a lens shape having an upward convex shape with a curved surface due to reflow processing, thereby forming the microlens 51.

Next, as illustrated in FIG. 13C, the first anti-reflective film 52 is formed on the entirety of the surface of the microlens 51. As the first anti-reflective film 52, for example, a silicon nitride film (SiN) or a silicon oxynitride film (SiON) can be formed by using a plasma CVD method. The film thickness of the first anti-reflective film 52 is set to a film thickness in a range of 90 to 155 nm (for example, 120 nm).

Next, as illustrated in FIG. 13D, the first anti-reflective film 52 of a pixel that is set to a single-layered anti-reflective film is removed by using dry etching and the like. In this embodiment, the first anti-reflective film 52 is not formed in two pixels of G among four pixels of G, R, B, and G which constitute the repetitive unit in the Bayer array, and only the second anti-reflective film 53 is formed. Accordingly, the first anti-reflective film 52 of a pixel of G is removed in FIG. 13D.

Next, as illustrated in FIG. 13E, the second anti-reflective film 53 is formed on an upper surface of the microlens 51 in the pixel of G, and on an upper surface of the first anti-reflective film 52 in the pixels of R and B. As the second anti-reflective film 53, for example, a silicon oxide film (SiO) or a silicon oxycarbide film (SiOC) can be formed, for example, by using the plasma CVD method. The film thickness of the second anti-reflective film 53 is set to a film thickness in a range of 60 to 100 nm (for example, 80 nm).

As described above, among the entirety of pixels of a pixel array in which the pixels are two-dimensionally arrayed, in a predetermined pixel (for example, a pixel of G), the single-layered anti-reflective film (the second anti-reflective film 53) is formed on the surface of the microlens 51, and in the other pixels (for example, a pixel of R and a pixel of B), the double-layered anti-reflective film (the first anti-reflective film 52 and the second anti-reflective film 53) is formed. Thus, the rear surface irradiation-type solid-state imaging element 50 illustrated in FIG. 9 is completed.

<Another Pixel Arrangement Example of Single-Layered Anti-Reflective Film>

In the above-described embodiment, two pixels of G among four pixels of G, R, B, and G which constitute a repetitive unit in a Bayer array are set to pixels in which the single-layered anti-reflective film (the second anti-reflective film 53) is formed, and a pixel of R and a pixel of B are set to pixels in which the double-layered anti-reflective film (the first anti-reflective film 52 and the second anti-reflective film 53) is formed.

However, an arrangement of pixels which are set to the single-layered anti-reflective film is not limited to the example, and other arrangements can be employed.

Figure 14:
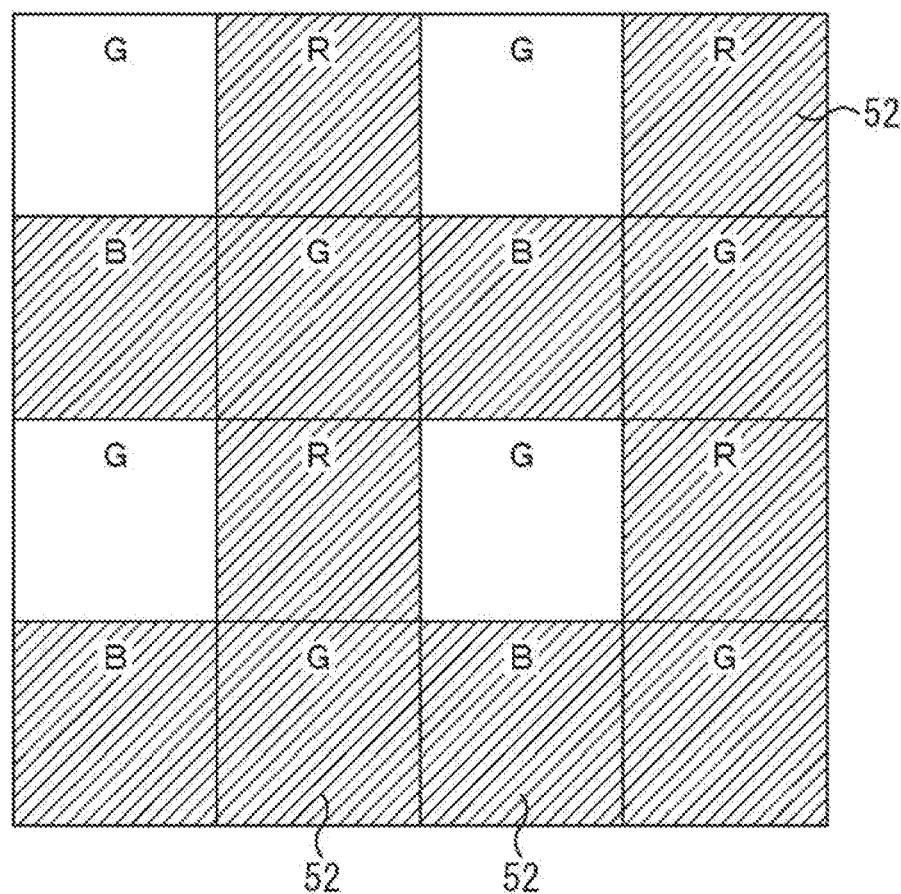

For example, as illustrated in FIG. 14, it is possible to employ an arrangement in which only one pixel of G among four pixels of G, R, B, and G which constitute the repetitive unit in the Bayer array are set to the single-layered anti-reflective film (the second anti-reflective film 53 alone). FIG. 14 is a plan view illustrating a pixel arrangement in which the first anti-reflective film 52 is formed as in FIG. 10. A pixel in which the first anti-reflective film 52 is not formed becomes a pixel in which only the second anti-reflective film 53 is formed.

As described above, in a case where one pixel of G among four pixels which constitute the repetitive unit in the Bayer array is set to a pixel in which only the second anti-reflective film 53 is formed, in comparison to a case where the two pixels of G among the four pixels of the repetitive unit are set to a pixel in which only the second anti-reflective film 53 is formed as illustrated in FIG. 10, the number of pixels having moisture permeability, that is, the number of pixels in which the anti-reflective film is formed in a single layer is reduced to the half. Therefore, the moisture permeability is reduced to the half, but a ratio of pixels in which the double-layered anti-reflective film is formed increases. As a result, it is possible to enhance the effect of suppressing occurrence of flares, ghosts, and color-mixing.

Figure 15:
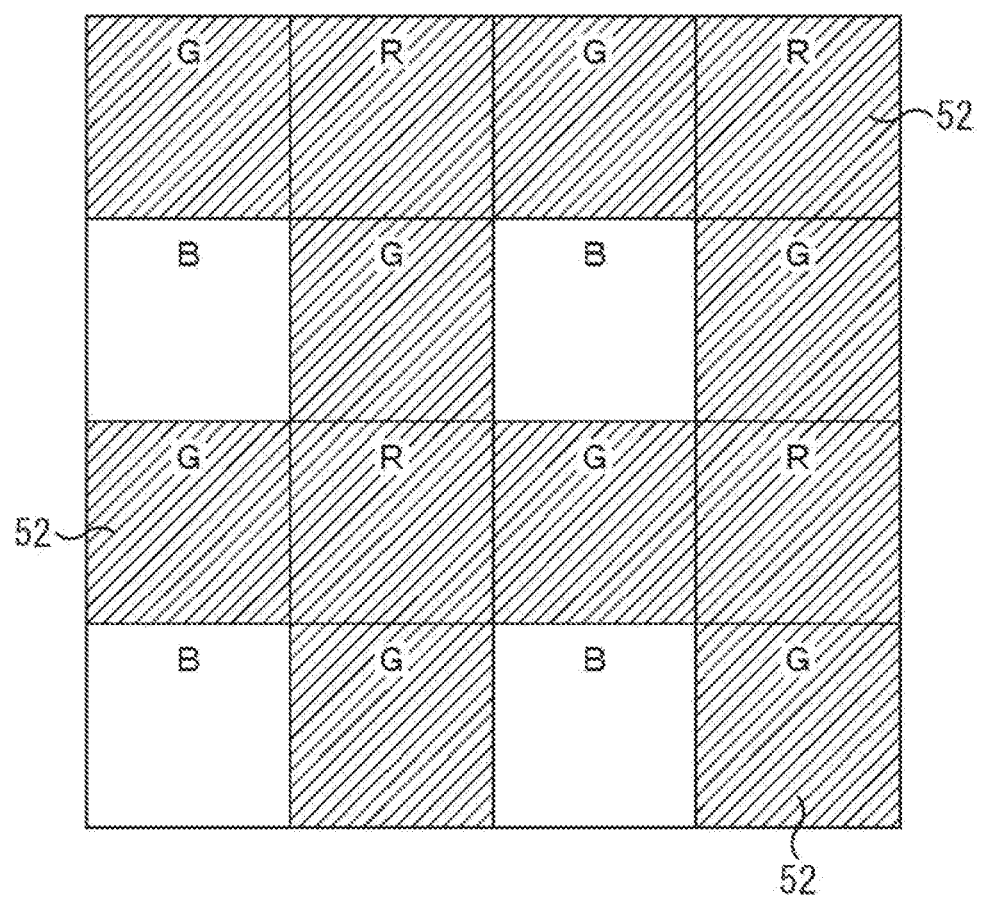

In addition, for example, as illustrated in FIG. 15, it is also possible to employ an arrangement in which only one pixel of B among four pixels of G, R, B, and G which constitute the repetitive unit in the Bayer array is set to the single-layered anti-reflective film (the second anti-reflective film 53 alone). FIG. 15 is a plan view illustrating a pixel arrangement in which the first anti-reflective film 52 is formed as in FIG. 10. A pixel in which the first anti-reflective film 52 is not formed becomes a pixel in which only the second anti-reflective film 53 is formed. In the entirety of pixels of a pixel array in which the pixels are two-dimensionally arrayed, all pixels of B become pixels in which the single-layered anti-reflective film (the second anti-reflective film 53 alone) is formed on the surface of the microlens 51.

Figure 16:
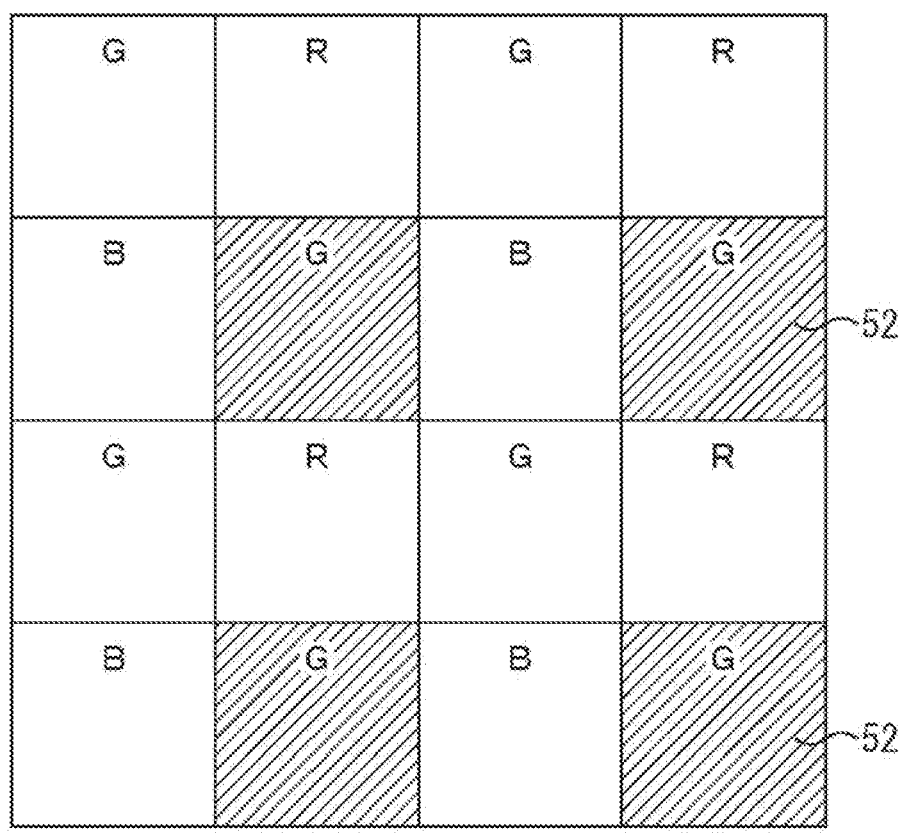

In addition, for example, as illustrated in FIG. 16, it is possible to employ an arrangement in which one pixel of each of R, G, and B among four pixels of G, R, B, and G which constitute the repetitive unit in the Bayer array are set to the single-layered anti-reflective film (the second anti-reflective film 53 alone). FIG. 16 is a plan view illustrating a pixel arrangement in which the first anti-reflective film 52 is formed as in FIG. 10. A pixel in which the first anti-reflective film 52 is not formed becomes a pixel in which only the second anti-reflective film 53 is formed.

As described above, in a case where an array of color filters is the Bayer array, at least one pixel among four pixels of G, R, B, and G which constitute the repetitive unit in the Bayer array is set to a pixel in which the single-layered anti-reflective film (the second anti-reflective film 53 alone) is formed. In this case, at least pixels corresponding to one-fourth of the number of the entirety of pixels of a pixel array in which pixels are two-dimensionally arrayed become pixels in which the single-layered anti-reflective film is formed on the surface of the microlens 51.

When increasing a ratio of pixels set to the single-layered anti-reflective film (the second anti-reflective film 53 alone) with respect to the number of the entirety of pixels of a pixel array in which pixels are two-dimensionally arrayed, moisture permeability is improved, and thus the effect of suppressing occurrence of stains is enhanced. On the other hand, when increasing a ratio of pixels set to the double-layered anti-reflective film (the first anti-reflective film 52 and the second anti-reflective film 53), the effect of suppressing occurrence of flares, ghosts, and color-mixing is enhanced.

The effect of suppressing occurrence of stains, and the effect of suppressing occurrence of flares, ghosts, and color-mixing have a trade-off relationship, and thus a numerical ratio between pixels set to the single-layered anti-reflective film (the second anti-reflective film 53 alone) and pixels set to the double-layered anti-reflective film (the first anti-reflective film 52 and the second anti-reflective film 53) may be determined in correspondence with a use of the rear surface irradiation-type solid-state imaging element 50 and the like.

<Application Example of Electronic Device>

The present technology is not limited to application to a solid-state imaging element. That is, the present technology is also applicable to the entirety of electronic devices, which use the solid-state imaging element in an image fetching unit (photoelectric conversion unit), such as an imaging device including a digital still camera, a video camera, and the like, a portable terminal device having an imaging function, and a copier that uses the solid-state imaging element in an image reading unit. The solid-state imaging element may employ an aspect in which the solid-state imaging element is formed as one chip, or a module-shaped aspect having an imaging function in which an imaging unit and a signal processing unit or an optical system are collectively packaged.

Figure 17:
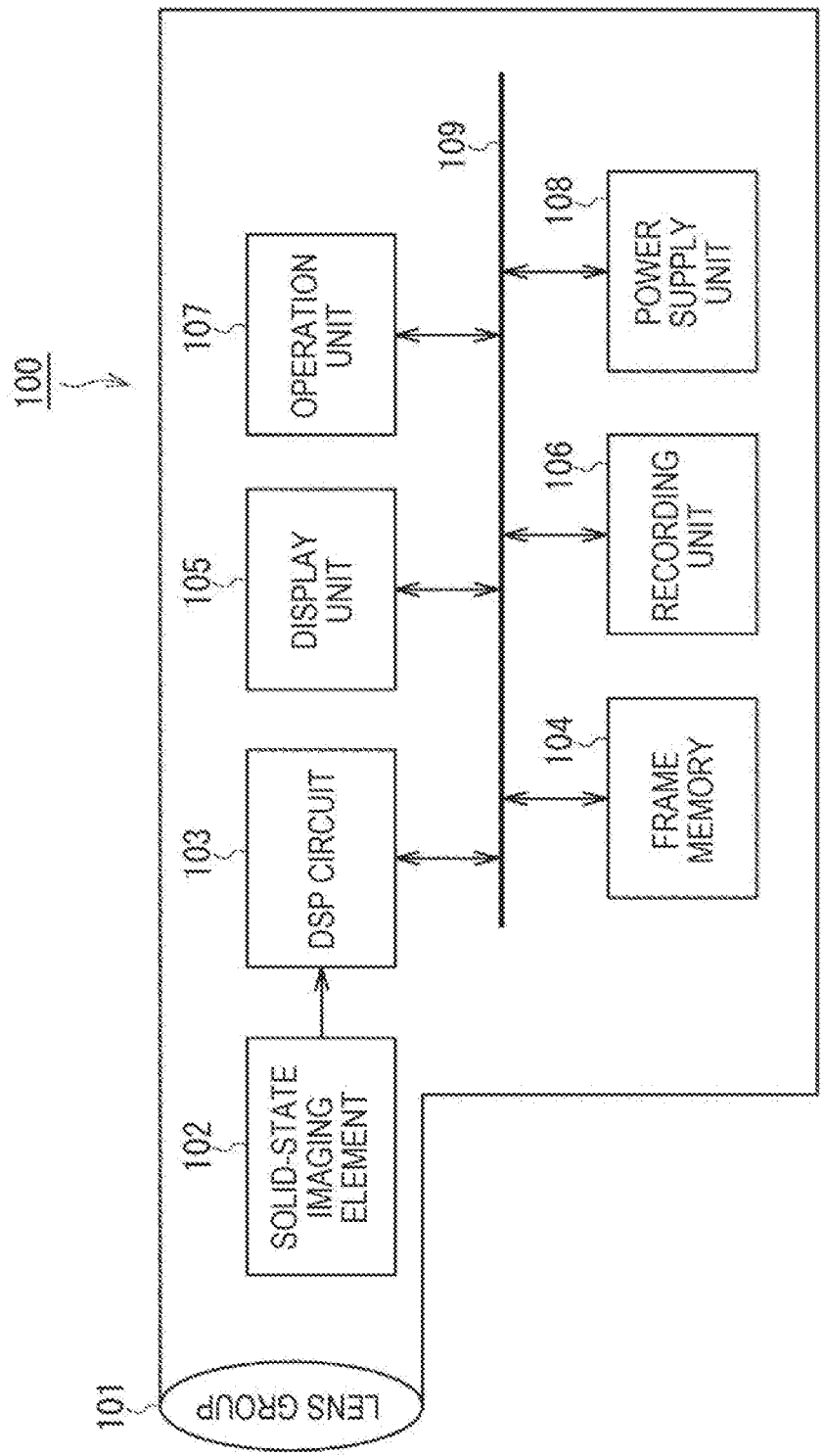

FIG. 17 is a block diagram illustrating a configuration example of an imaging device as an electronic device to which the present technology is applied.

An imaging device 100 in FIG. 17 includes an optical unit 101 including a lens group and the like, a solid-state imaging element (imaging device) 102 that employs the configuration of the rear surface irradiation-type solid-state imaging element 50 in FIG. 9, and a digital signal processor (DSP) circuit 103 that is a camera signal processing circuit. In addition, the imaging device 100 also includes a frame memory 104, a display unit 105, a recording unit 106, an operation unit 107, and a power supply unit 108. The DSP circuit 103, the frame memory 104, the display unit 105, the recording unit 106, the operation unit 107, and the power supply unit 108 are connected to each other through a bus line 109.

The optical unit 101 receives incident light (image light) from a subject and forms an image on an imaging plane of the solid-state imaging element 102. The solid-state imaging element 102 converts a light quantity of the incident light of which an image is formed on the imaging plane by the optical unit 101 into an electric signal in a pixel unit, and outputs the electric signal as a pixel signal. As the solid-state imaging element 102, it is possible to use the rear surface irradiation-type solid-state imaging element 50 in FIG. 9, that is, an solid-state imaging element including a pixel in which the single-layered anti-reflective film (the second anti-reflective film 53) is formed on the surface of the microlens 51, and a pixel in which the double-layered anti-reflective film (the first anti-reflective film 52 and the second anti-reflective film 53) is formed.

For example, the display unit 105 is constituted by a thin-type display such as a liquid crystal display (LCD) and an organic electroluminescence (EL) display, and displays a moving image or a still image which is captured by the solid-state imaging element 102. The recording unit 106 records the moving image or the still image which is captured by the solid-state imaging element 102 in a recording medium such as a hard disk and a semiconductor memory.

The operation unit 107 issues an operation command with respect to various functions of the imaging device 100 through an operation by a user. The power supply unit 108 appropriately supplies various kinds of power which become an operation power supply of the DSP circuit 103, the frame memory 104, the display unit 105, the recording unit 106, and the operation unit 107 to the supply targets.

As described above, when using the rear surface irradiation-type solid-state imaging element 50 as the solid-state imaging element 102, it is possible to reduce reflected light while suppressing occurrence of stains. Thus, it is possible to suppress occurrence of flares, ghosts, and color mixing, and it is also possible to suppress deterioration of sensitivity characteristics due to a gap of the microlens. As a result, even in the imaging device 100 such as a video camera, a digital still camera, and a camera module for a mobile device such as a portable telephone, it is possible to realize high image quality of a captured image.

<Use Example of Image Sensor>

Figure 18:
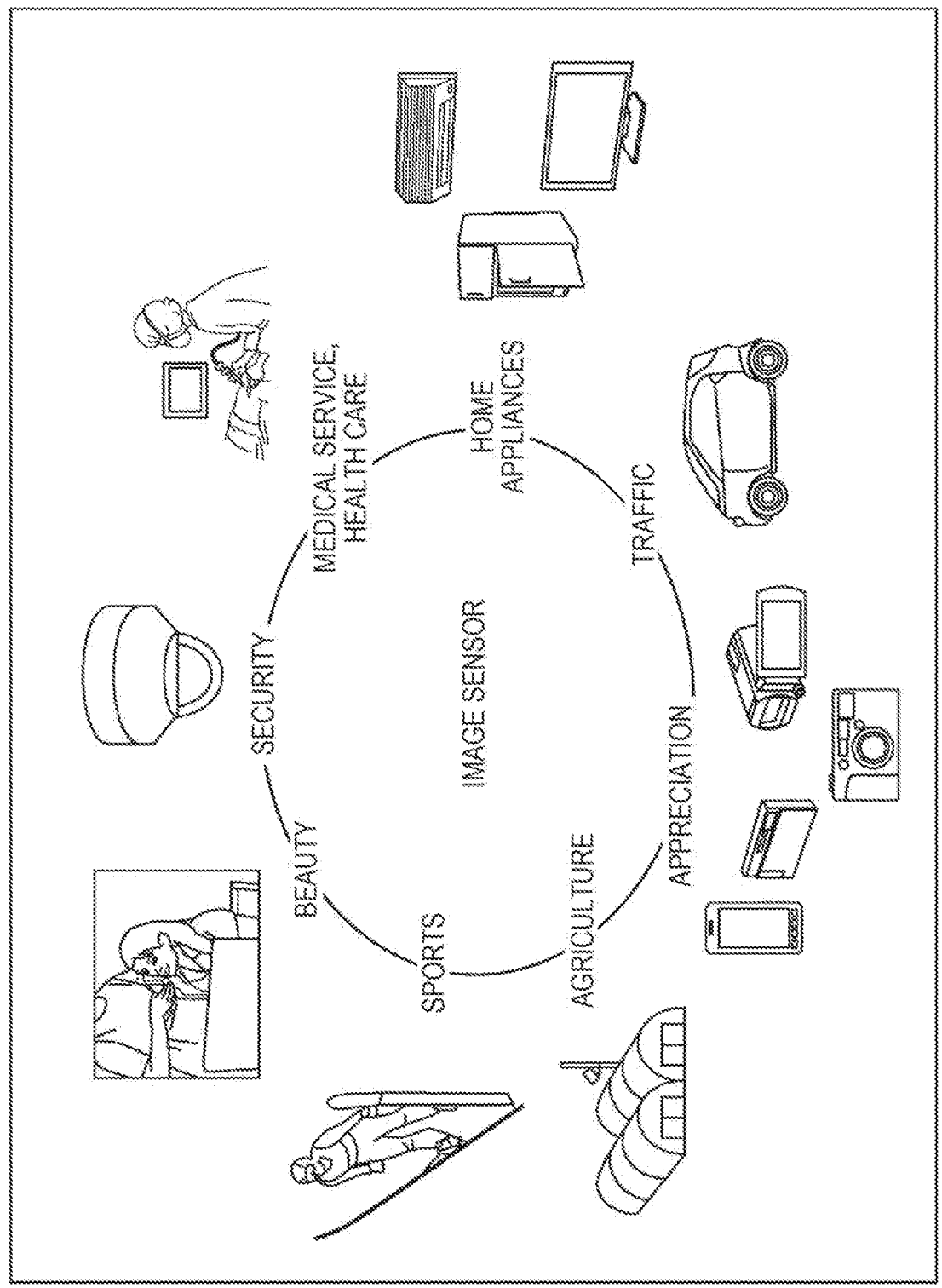

FIG. 18 is a diagram illustrating a use example of an image sensor that uses the rear surface irradiation-type solid-state imaging element 50.

The image sensor that uses the rear surface irradiation-type solid-state imaging element 50 can be used, for example, in various cases of sensing light such as visible light, infrared light, ultraviolet light, and X-rays as to be described below.

- Devices such as a digital camera and a camera function-equipped portable device which capture an image that is supplied for appreciation
- Devices, which a reapplied to a traffic use, such as a non-vehicle sensor that photographs a front side, a rear side, a periphery, the inside, and the like of a vehicle for safe driving such as automatic stopping, recognition of driver's state, and the like, a monitoring camera that monitors a traveling vehicle or a road, and a distance measurement sensor that measures a distance between vehicles, and the like
- Devices which are applied to home appliances such as a TV, a refrigerator, and an air conditioner to photograph a gesture of a user and to perform a device operation in accordance with the gesture
- Devices, which are applied to a use of medical service and health care, such as an endoscope and a device that performs a blood vessel photographing through reception of infrared light
- Devices such as a security monitoring camera, a person authentication camera, and the like which are applied to a use of security
- Devices, which are applied to a use of beauty, such as a skin measurement device that photographs a skin, and a microscope that photographs a head skin
- Devices such as a sport action camera and a wearable camera which are applied to a use of sports or the like
- Devices such as a camera that monitors a state of fields or plants which are applied to a use of agriculture First Application Example The technology of the present disclosure is applicable to various products. For example, the technology of the present disclosure may be applied to patient in-body information acquisition system that uses a capsule-type endoscope.

Figure 19:
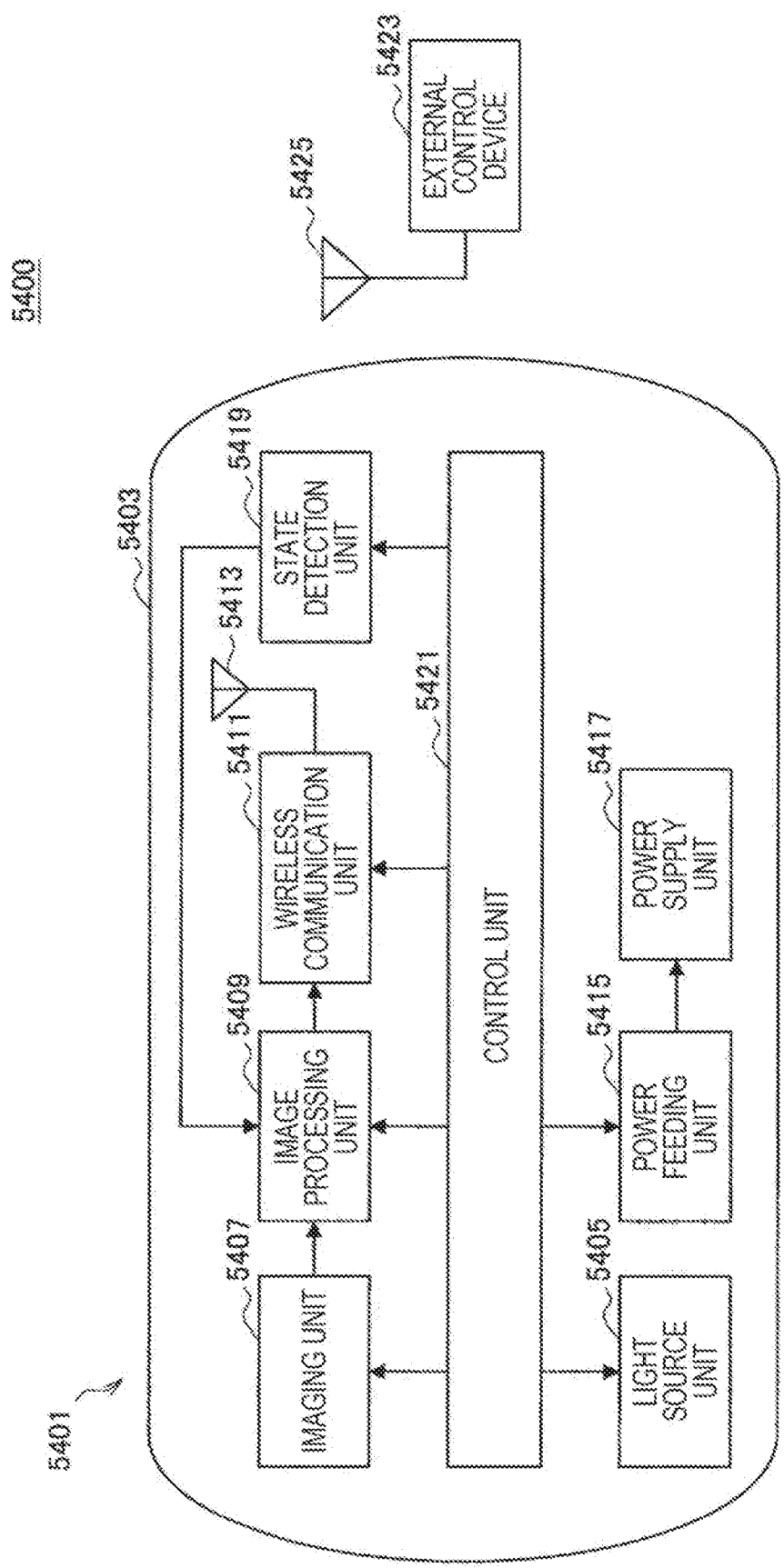

FIG. 19 is a diagram illustrating an example of a schematic configuration of an in-body information acquisition system 5400 to which the technology according to the present disclosure is applicable. When referring to FIG. 19, the in-body information acquisition system 5400 includes a capsule-type endoscope 5401, and an external control device 5423 that collectively controls an operation of the in-body information acquisition system 5400. In inspection, the capsule-type endoscope 5401 is swallowed by a patient. The capsule-type endoscope 5401 has an imaging function and a wireless communication function, sequentially captures images of the inside of organs (hereinafter, also referred to as an in-body image) at a predetermined interval while moving at the inside of organs such as the stomach and bowels through a peristaltic motion or the like until being naturally discharged from the patient, and sequentially transmits information related to the in-body image to the external control device 5423 at the outside of the body in a wireless manner. The external control device 5423 generates image data for displaying the in-body image on a display device (not illustrated) on the basis of the information related to the in-body image that is received. In the in-body information acquisition system 5400, it is possible to regularly obtain an image that is obtained by capturing an in-body state image of a patient until the capsule-type endoscope 5401 is discharged after being swallowed.

A configuration and a function of the capsule-type endoscope 5401 and the external control device 5423 will be described in more detail. As illustrated in the drawing, the capsule-type endoscope 5401 is constituted by mounting functions of a light source unit 5405, an imaging unit 5407, an image processing unit 5409, a wireless communication unit 5411, a power feeding unit 5415, a power supply unit 5417, a state detection unit 5419, and a control unit 5421 in a capsule-type housing 5403.

For example, the light source unit 5405 is constituted by a light source such as a light emitting diode (LED), and irradiates an imaging visual field of the imaging unit 5407 with light.

The imaging unit 5407 is constituted by an optical system including an imaging element and a plurality of lenses which are provided at a front stage of the imaging element. Reflected light of light that is emitted to a body tissue that is an observation target (hereinafter, referred to as observation light) is condensed to the optical system, and is incident to the imaging element. The imaging element receives the observation light and performs photoelectric conversion of the observation light to generate an electric signal corresponding to the observation light, that is, an image signal corresponding to an observation image. The image signal generated by the imaging unit 5407 is supplied to the image processing unit 5409. Furthermore, as an imaging element of the imaging unit 5407, various known imaging elements such as a complementary metal oxide semiconductor (CMOS) image sensor and a charge coupled device (CCD) image sensor may be used.

The image processing unit 5409 is constituted by a processor such as a central processing unit (CPU) and a graphics processing unit (GPU), and performs various kinds of signal processing with respect to the image signal that is generated by the imaging unit 5407. The various kinds of signal processing may be minimum processing for transmitting the image signal to the external control device 5423 (for example, compression of the image data, conversion of a frame rate, conversion of a data rate and/or conversion of a format, and the like). Since the image processing unit 5409 is configured to perform only necessary minimum processing, the image processing unit 5409 can be realized in a smaller size and at lower power consumption. As a result, the image processing unit 5409 is compatible with the capsule-type endoscope 5401. However, in a case where there is a margin for a space in the housing 5403 and power consumption, another signal processing (for example, noise removal processing, another high image quality processing, and the like) may be performed in the image processing unit 5409. The image processing unit 5409 supplies the image signal to which the signal processing is performed to the wireless communication unit 5411 as RAW data. Furthermore, in a case where information related to a state (movement, posture, and the like) of the capsule-type endoscope 5401 is acquired by the state detection unit 5419, the image processing unit 5409 may supply the image signal to the wireless communication unit 5411 in correlation with the information. Thus, a position in a body in which the image is captured, an imaging direction of the image, and the like, and the captured image can be correlated with each other.

The wireless communication unit 5411 is constituted by a communication device that can transmit and receive various pieces of information to and from the external control device 5423. The communication device is constituted by an antenna 5413, a processing circuit that performs modulation processing for transmission and reception of a signal and the like, and the like. The wireless communication unit 5411 performs predetermined processing such as modulation processing with respect to the image signal to which signal processing is performed by the image processing unit 5409, and transmits the image signal to the external control device 5423 through the antenna 5413. In addition, the wireless communication unit 5411 receives a control signal related to driving control of the capsule-type endoscope 5401 from the external control device 5423 through the antenna 5413. The wireless communication unit 5411 supplies the received control signal to the control unit 5421.

The power feeding unit 5415 is constituted by an antenna coil for power reception, a power reproduction circuit that reproduces electric power from a current that occurs in the antenna coil, a booster circuit, and the like. In the power feeding unit 5415, electric power is generated by using a so-called non-contact charging principle. Specifically, when a magnetic field (electromagnetic wave) of a predetermined frequency is applied to the antenna coil of the power feeding unit 5415 from an outer side, an induced electromotive force occurs in the antenna coil. For example, the electromagnetic wave may be a carrier wave that is transmitted from the external control device 5423 through the antenna 5425. Electric power is reproduced from the induced electromotive force by the power reproduction circuit, and a potential thereof is appropriately adjusted in the booster circuit. Thus, electric power for electricity storage is generated. The electric power generated by the power feeding unit 5415 is stored in the power supply unit 5417.

The power supply unit 5417 is constituted by a secondary battery and stores electric power that is generated by the power feeding unit 5415. In FIG. 19, an arrow indicating an electric power supply destination from the power supply unit 5417, and the like are not illustrated to avoid complication of the drawing, but the electric power stored in the power supply unit 5417 is supplied to the light source unit 5405, the imaging unit 5407, the image processing unit 5409, the wireless communication unit 5411, the state detection unit 5419, and the control unit 5421, and can be used for driving thereof.

The state detection unit 5419 is constituted by a sensor such as an acceleration sensor and/or a gyro sensor which detects a state of the capsule-type endoscope 5401. The state detection unit 5419 can acquire information related to the state of the capsule-type endoscope 5401 from the detection result by the sensor. The state detection unit 5419 supplies the acquired information related to the state of the capsule-type endoscope 5401 to the image processing unit 5409. As described above, in the image processing unit 5409, the information related to the state of the capsule-type endoscope 5401 can be correlated with the image signal.

The control unit 5421 is constituted by a processor such as a CPU and operates in accordance with a predetermined program to collectively control an operation of the capsule-type endoscope 5401. The control unit 5421 appropriately controls driving of the light source unit 5405, the imaging unit 5407, the image processing unit 5409, the wireless communication unit 5411, the power feeding unit 5415, the power supply unit 5417, and the state detection unit 5419 in accordance with a control signal transmitted from the external control device 5423, thereby realizing the functions in the respective units as described above.

The external control device 5423 may be a processor such as a CPU and a GPU, a micro computer or a control substrate in which a processor and a storage element such as a memory are mixed in, or the like. The external control device 5423 includes the antenna 5425, and is configured to transmit and receive various pieces of information to and from the capsule-type endoscope 5401 through the antenna 5425. Specifically, the external control device 5423 controls an operation of the capsule-type endoscope 5401 by transmitting a control signal to the control unit 5421 of the capsule-type endoscope 5401. For example, light irradiation conditions with respect to an observation target in the light source unit 5405 may be changed by the control signal transmitted from the external control device 5423. In addition, imaging conditions (for example, a frame rate, an exposure value, and the like in the imaging unit 5407) may be changed by the control signal transmitted from the external control device 5423. In addition, processing contents in the image processing unit 5409, or image signal transmission conditions (for example, a transmission interval, the number of transmission images, and the like) of the wireless communication unit 5411 may be changed by the control signal transmitted from the external control device 5423.

In addition, the external control device 5423 performs various kinds of image processing with respect to the image signal that is transmitted from the capsule-type endoscope 5401, and generates image data for displaying the in-body image that is captured on the display device. As the image processing, for example, various kinds of known signal processing such as development processing (demosaic processing) high image quality processing (band emphasis processing, ultra resolution processing, noise reduction (NR) processing and/or image stabilization processing, and the like), and/or enlargement processing (electronic zoom processing) may be performed. The external control device 5423 controls driving of the display device (not illustrated) to display the captured in-body image on the basis of the generated image data. Alternatively, the external control device 5423 may cause a recording device (not illustrated) to record the generated image data, or may cause a printing device (not illustrated) to print out the generated image data.

Hereinbefore, an example of the in-body information acquisition system 5400 to which the technology according to the present disclosure is applicable has been described. The technology according to the present disclosure is appropriately applicable to the imaging unit 5407 among the above-described configurations. Specifically, the rear surface irradiation-type solid-state imaging element 50 in FIG. 9 is also applicable to the imaging unit 5407. When the rear surface irradiation-type solid-state imaging element 50 in FIG. 9 is applied to the imaging unit 5407, it is possible to obtain a clearer image of an operation part, and thus inspection accuracy is improved.

Second Application Example

The technology according to the present disclosure may be realized, for example, as a device that is mounted on any one kind of moving body among an automobile, an electric vehicle, a hybrid electric vehicle, a motorcycle, a bicycle, a personal mobility, an airplane, a drone, a ship, a robot, a construction machine, an agricultural machine (tractor), and the like.

Figure 20:
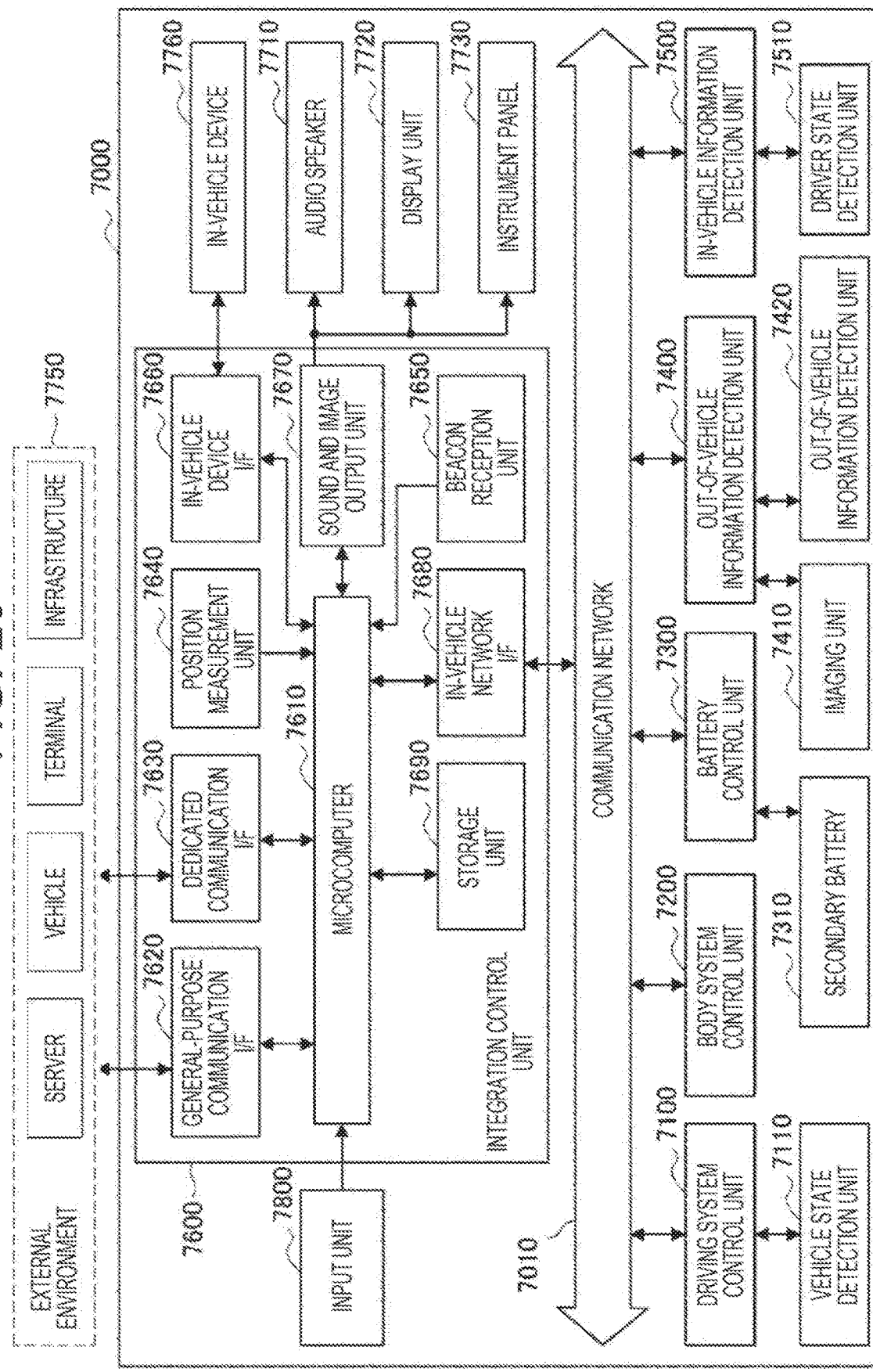

FIG. 20 i s a block diagram illustrating a schematic configuration example of a vehicle control system 7000 that is an example of a moving body control system to which the technology according to the disclosure is applicable. The vehicle control system 7000 includes a plurality of electronic control units which are connected to each other through a communication network 7010. In the example illustrated in FIG. 20, the vehicle control system 7000 includes a driving system control unit 7100, a body system control unit 7200, a battery control unit 7300, an out-of-vehicle information detection unit 7400, an in-vehicle information detection unit 7500, and an integration control unit 7600. For example, the communication network 7010 that connects the plurality of control units to each other may be an on-vehicle communication network according to arbitrary standards such as a controller area network (CAN), a local interconnect network (LIN), a local area network (LAN), and FlexRay (registered trademark).

The respective control units include a microcomputer that performs operation processing according to various programs, a storage unit that stores a program that is executed by the microcomputer, parameters capable of being used in various operations, and the like, and a drive circuit that drives devices of various control targets. Each of the respective control units includes a network I/F for performing communication with the other control units through the communication network 7010, and includes a communication I/F for performing communication with devices, sensors, and the like which are located on an inner side and on an outer side of a vehicle through wired communication or wireless communication. In FIG. 20, as a functional configuration of the integration control unit 7600, a microcomputer 7610, a general-purpose communication I/F 7620, a dedicated communication I/F 7630, a position measurement unit 7640, a beacon reception unit 7650, an in-vehicle device I/F 7660, a sound and image output unit 7670, an on-vehicle network I/F 7680, and a storage unit 7690 are illustrated in the drawing. Similarly, other control units also include a microcomputer, a communication I/F, a storage unit, and the like.

The driving system control unit 7100 controls an operation of devices related to a driving system of a vehicle in accordance with various programs. For example, the driving system control unit 7100 functions as a control device of a driving force generation device such as an internal combustion engine and a driving motor which generate a driving force of a vehicle, a driving force transmission mechanism that transmits the driving force to wheels, a steering mechanism that adjusts a steering angle of the vehicle, a braking device that generates a braking force of the vehicle, and the like. The driving system control unit 7100 may have a function as a control device of an antilock brake system (ABS), an electronic stability control (ESC), and the like.

A vehicle state detection unit 7110 is connected to the driving system control unit 7100. For example, the vehicle state detection unit 7110 includes at least one of a gyro sensor that detects an angular velocity of an axial rotary motion of a vehicle body, an acceleration sensor that detects an acceleration of the vehicle, or sensors which detect an operation amount of an accelerator pedal, an operation amount of a brake pedal, a steering angle of a steering wheel, the number of engine revolutions, a rotation speed of a wheel, and the like. The driving system control unit 7100 performs operation processing by using a signal that is input from the vehicle state detection unit 7110, and controls an internal combustion engine, a driving motor, an electric power steering device, a brake device, and the like.

The body system control unit 7200 controls an operation of various devices which are mounted on the vehicle body in accordance with various programs. For example, the body system control unit 7200 functions as a control device of a keyless entry system, a smart key system, a power window device, and various lamps such as a head lamp, a back lamp, a brake lamp, a winker, and a fog lamp. In this case, an electric wave transmitted from a portable device that substitutes for a key, or signals of various switches may be input to the body system control unit 7200. The body system control unit 7200 receives input of the electric wave or the signals, and controls a door lock device, a power window device, the lamps, and the like of the vehicle.

The battery control unit 7300 controls a secondary battery 7310 that is a power supply source of the driving motor in accordance with various programs. For example, information such as a battery temperature, a battery output voltage, and a battery residual capacity is input from a battery device including the secondary battery 7310 to the battery control unit 7300. The battery control unit 7300 performs operation processing by using the signals, and performs temperature adjustment control of the secondary battery 7310, and control of a cooling device and the like that is provided in the battery device.

The out-of-vehicle information detection unit 7400 detects external information of the vehicle on which the vehicle control system 7000 is mounted. For example, at least one of an imaging unit 7410 or an out-of-vehicle information detection unit 7420 is connected to the out-of-vehicle information detection unit 7400. The imaging unit 7410 includes at least one among a time of flight (ToF) camera, a stereo camera, a monocular camera, an infrared camera, and other cameras. For example, the out-of-vehicle information detection unit 7420 includes at least one among an environment sensor that detects current weather or meteorological phenomena, and a nearby information detection sensor that detects other vehicles at the periphery of the vehicle on which the vehicle control system 7000 is mounted, obstacles, pedestrians, and the like.

For example, the environment sensor may be at least one among a raindrop sensor that detects rainy weather, a fog sensor that detects fog, a sunshine sensor that detects the degree of sunshine, and a snow sensor that detects snowfall. The nearby information detection sensor may be at least one among an ultrasonic sensor, a radar device, and a light detection and ranging, laser imaging detection and ranging (LIDAR) device. The imaging unit 7410 and the out-of-vehicle information detection unit 7420 may be provided as an independent sensor or device, or as a device in which a plurality of sensors or devices are integrated.

Figure 21:
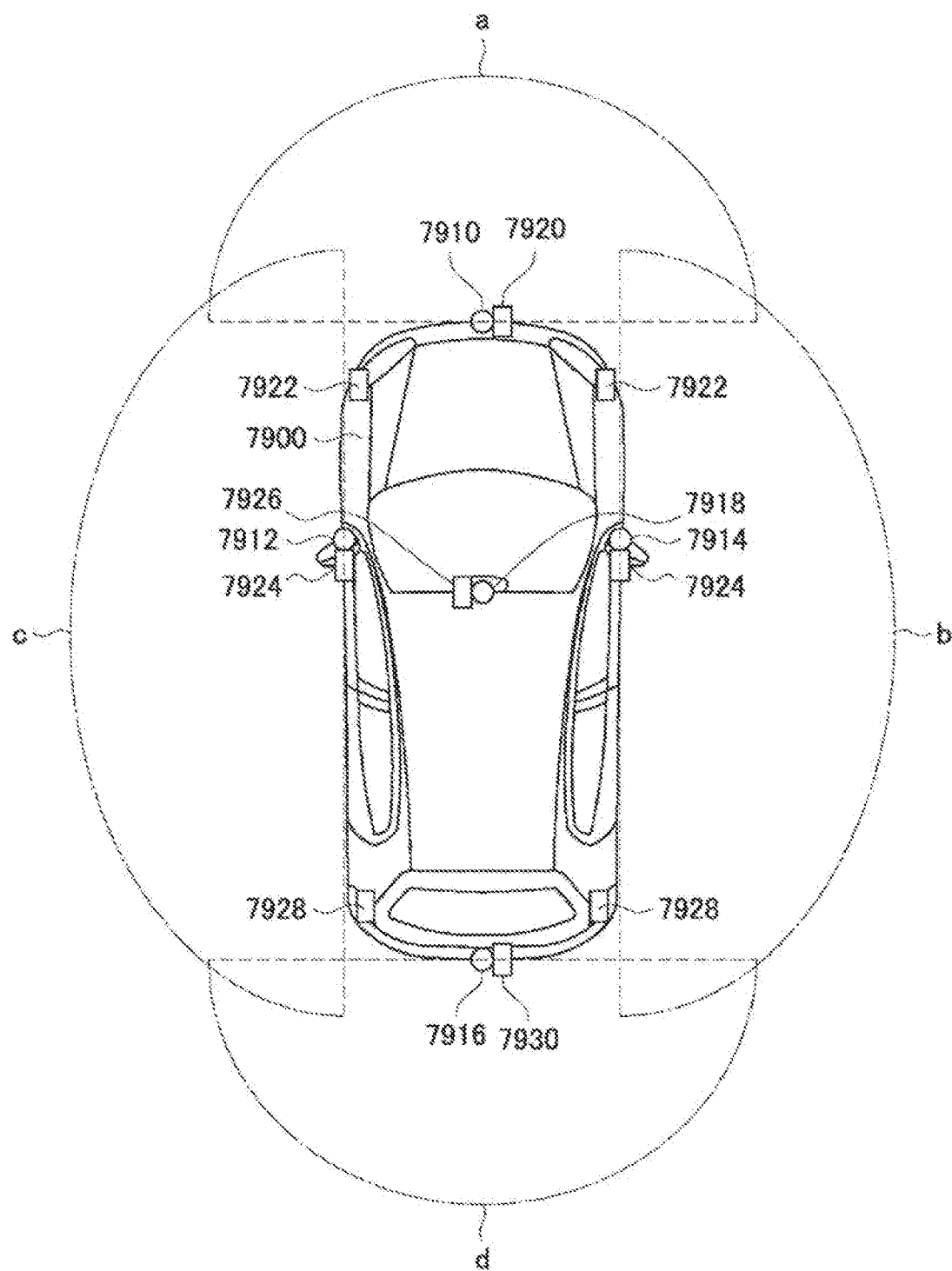

Here, FIG. 21 illustrates an example of an installation position of the imaging unit 7410 and the out-of-vehicle information detection unit 7420. For example, each of imaging units 7910, 7912, 7914, 7916, and 7918 is provided at least at one position among a front nose, a side-view mirror, a rear bumper, a back door, and an upper portion of an in-vehicle windshield glass of a vehicle 7900. The imaging unit 7910 that is provided in the front nose, and the imaging unit 7918 that is provided in the upper portion of the in-vehicle windshield glass mainly acquire an image in front of the vehicle 7900. The imaging units 7912 and 7914 which are provided in the side-view mirrors mainly acquire an image on a lateral side of the vehicle 7900. The imaging unit 7916 that is provided in the rear bumper or the back door mainly acquires an image on a rear side of the vehicle 7900. The imaging unit 7918 that is provided on the upper portion of the in-vehicle windshield glass is mainly used for detection of a preceding vehicle, a pedestrian, an obstacle, a traffic signal, a traffic board, a lane, and the like.

Furthermore, FIG. 21 illustrates an example of an imaging range of the respective imaging units 7910, 7912, 7914, and 7916. An imaging range a represents an imaging range of the imaging unit 7910 that is provided in the front nose, imaging ranges b and c represent imaging ranges of the imaging units 7912 and 7914 which are provided in the side-view mirrors, and an imaging range d represents an imaging range of the imaging unit 7916 that is provided in the rear bumper or the back door. For example, when pieces of image data which are captured by the imaging units 7910, 7912, 7914, and 7916 overlap each other, an overhead view image when the vehicle 7900 is viewed from an upward side of the vehicle 7900 is obtained.

Out-of-vehicle information detection units 7920, 7922, 7924, 7926, 7928, and 7930 which are provided in a front, a rear, sides, corners, and an upper portion of the in-vehicle windshield glass of the vehicle 7900 may be, for example, an ultrasonic sensor or a radar device. The out-of-vehicle information detection units 7920, 7926, and 7930 which are provided in the front nose, the rear bumper, the back door, and an upper portion of the in-vehicle windshield glass of the vehicle 7900 may be, for example, the LIDAR device. The out-of-vehicle information detection units 7920 to 7930 are mainly used for detection of a preceding vehicle, a pedestrian, an obstacle, and the like.

Description will continue with reference to FIG. 20. The out-of-vehicle information detection unit 7400 causes the imaging unit 7410 to capture an out-of-vehicle image, and receives captured image data. In addition, the out-of-vehicle information detection unit 7400 receives detection information from the out-of-vehicle information detection unit 7420 that is connected to the out-of-vehicle information detection unit 7400. In a case where the out-of-vehicle information detection unit 7420 is the ultrasonic sensor, the radar device, or the LIDAR device, the out-of-vehicle information detection unit 7400 transmits an ultrasonic wave, an electromagnetic wave, and the like, and receives information of a reflected wave that is received. The out-of-vehicle information detection unit 7400 may perform object detection processing of a person, a vehicle, an obstacle, a sign, a character on a road surface, and the like, or distance detection processing on the basis of received information. The out-of-vehicle information detection unit 7400 may perform environment recognition processing of recognizing raindrop, fog, a road surface situation, and the like on the basis of the received information. The out-of-vehicle information detection unit 7400 may calculate a distance to an out-of-vehicle object on the basis of the received information.

In addition, the out-of-vehicle information detection unit 7400 may perform image recognition processing of recognizing a person, a vehicle, an obstacle, a sign, a character on a load surface, and the like, or distance detection processing on the basis of received image data. The out-of-vehicle information detection unit 7400 may perform processing such as distortion correction, alignment, and the like with respect to received image data, and may combine pieces of image data captured by the other imaging unit 7410 to generate an overhead view image or a panoramic image. The out-of-vehicle information detection unit 7400 may perform visual point conversion processing by using image data captured by the other imaging unit 7410.

The in-vehicle information detection unit 7500 detects in-vehicle information. For example, a driver state detection unit 7510 that detects a driver state is connected to the in-vehicle information detection unit 7500. The driver state detection unit 7510 may include a camera that captures an image of a driver, a biological sensor that detects biological information of the driver, a microphone that collects an in-vehicle sound, and the like. For example, the biological sensor is provided on a seating surface, a steering wheel, and the like, and detects biological information of an occupant who sits on a seat, or a driver who grips the steering wheel. The in-vehicle information detection unit 7500 may calculate the degree of fatigue or the degree of concentration of the driver, or may determine whether or not the driver falls asleep on the basis of detection information that is input from the driver state detection unit 7510. The in-vehicle information detection unit 7500 may perform processing such as noise cancellation processing with respect to a sound signal that is collected.

The integration control unit 7600 controls whole operations in the vehicle control system 7000 in accordance with various programs. An input unit 7800 is connected to the integration control unit 7600. For example, the input unit 7800 is realized by devices such as a touch panel, a button, a microphone, a switch, and a lever which are subjected to input operation by an occupant. Data obtained through sound recognition of a sound that is input by the microphone may be input to the integration control unit 7600. For example, the input unit 7800 may be a remote control device using infrared rays or other electric waves, or an external connection device such as a portable telephone or a personal digital assistant (PDA) which corresponds to an operation of the vehicle control system 7000. For example, the input unit 7800 may be a camera, and in this case, an occupant can input information with a gesture. Alternatively, data obtained by detecting movement of a wearable device which the occupant wears may be input. In addition, for example, the input unit 7800 may include an input control circuit that generates an input signal on the basis of information input by the occupant and the like by using the input unit 7800, and outputs the input signal to the integration control unit 7600, and the like. The occupant and the like operate the input unit 7800 to input various pieces of data to the vehicle control system 7000 or to instruct the vehicle control system 7000 to perform a processing operation.

The storage unit 7690 may include a read only memory (ROM) that stores various programs which are executed by the microcomputer, and a random access memory (RAM) that stores various parameters, operation results, sensor values, and the like. In addition, the storage unit 7690 may be realized by a magnetic storage device such as a hard disc drive (HDD), a semiconductor storage device, an optical storage device, a magneto-optical storage device, and the like.

The general-purpose communication I/F 7620 is a general-purpose communication I/F that relays communication with various devices which exist in an external environment 7750. In the general-purpose communication I/F 7620, a cellular communication protocol such as Global System of Mobile communications (GSM) (registered trademark), WiMAX (registered trademark), Long Term Evolution (LTE) (registered trademark), and LTE-Advanced (LTE-A), and other wireless communication protocols such as a wireless LAN (also referred to as Wi-Fi (registered trademark)), and Bluetooth (registered trademark) may be embedded. For example, the general-purpose communication I/F 7620 may be connected to a device (for example, an application server or a control server) that exists on an external network (for example, the Internet, a cloud network, or a company-specific network) through a base station or an access point. In addition, the general-purpose communication I/F 7620 may be connected to a terminal that exists in the vicinity of a vehicle (for example, a terminal of a driver, a pedestrian, or a shop, or a machine type communication (MTC) terminal), for example, by using a peer to peer (P2P) technology.

The dedicated communication I/F 7630 is a communication I/F that supports a communication protocol that is designed for a use in a vehicle. In the dedicated communication I/F 7630, for example, a standard protocol such as a wireless access in vehicle environment (WAVE) that is a combination of IEEE 802.11p of a lower layer and IEEE1609 of a higher layer, dedicated short range communications (DSRC), and a cellular communication protocol may be embedded. Typically, the dedicated communication I/F 7630 performs V2X communication that is a concept including one or more among vehicle to vehicle communication, vehicle to infrastructure communication, vehicle to home communication, and vehicle to pedestrian communication.

For example, the position measurement unit 7640 executes position measurement by receiving a global navigation satellite system (GNSS) signal from a GNSS satellite (for example, a global positioning system (GPS) signal from a GPS satellite), and generates position information including a latitude, a longitude, and an altitude of the vehicle. Furthermore, the position measurement unit 7640 may specify a current position through signal exchange with a wireless access point, or may acquire position information from a terminal such as a portable telephone, a PHS, or a smartphone which has a position measurement function.

For example, the beacon reception unit 7650 receives an electric wave or an electromagnetic wave which is transmitted from a wireless station that is provided on a road, and the like, and acquires information such as a current position, delay, closure to traffic, and a required time. Furthermore, a function of the beacon reception unit may be included in the dedicated communication I/F 7630.

The in-vehicle device I/F 7660 is a communication interface that relays connection between the microcomputer 7610 and various in-vehicle devices 7760. The in-vehicle device I/F 7660 may establish wireless connection by using a wireless communication protocol such as a wireless LAN, Bluetooth (registered trademark), near field communication (NFC), and a wireless USB (WUSB). In addition, the in-vehicle device I/F 7660 may establish wired connection such as a universal serial bus (USB), High-Definition Multimedia Interface (HDMI) (registered trademark), and a mobile high-definition link (MHL) through a connection terminal (and a cable as necessary) (not illustrated). For example, the in-vehicle devices 7760 may include at least one among mobile devices or wearable devices of occupants, and information devices which are conveyed into or mounted on a vehicle. In addition, the in-vehicle devices 7760 may include a navigation device that performs route searching to an arbitrary destination. The in-vehicle device I/F 7660 exchanges a control signal or a data signal with the in-vehicle devices 7760.

The on-vehicle network I/F 7680 is an interface that relays communication between the microcomputer 7610 and the communication network 7010. The on-vehicle network I/F 7680 transmits and receives a signal and the like on the basis of a predetermined protocol that is supported by the communication network 7010.

The microcomputer 7610 of the integration control unit 7600 controls the vehicle control system 7000 in accordance with various programs on the basis of information that is acquired through at least one among the general-purpose communication I/F 7620, the dedicated communication I/F 7630, the position measurement unit 7640, the beacon reception unit 7650, the in-vehicle device I/F 7660, and the on-vehicle network I/F 7680. For example, the microcomputer 7610 may calculate a control target value of the driving force generation device, the steering mechanism, or the braking device on the basis of acquired information on an inner side and on an outer side of a vehicle, and may output a control command with respect to the driving system control unit 7100. For example, the microcomputer 7610 may perform cooperative control to realize advanced driver assistance system (ADAS) functions including collision avoidance or impact mitigation of a vehicle, following travel based on an inter-vehicle distance, vehicle-speed maintaining travel, collision alarm of a vehicle, and vehicle lane departure alarm, and the like. In addition, the microcomputer 7610 may perform cooperative control to realize automatic driving and the like in which a vehicle autonomously travels without depending on a driver's operation by controlling the driving force generation device, the steering mechanism, the braking device, and the like on the basis of acquired nearby information of the vehicle.

The microcomputer 7610 may generate three-dimensional distance information between a vehicle and an object such as a nearby structure and a nearby person on the basis of information that is acquired through at least one among the general-purpose communication I/F 7620, the dedicated communication I/F 7630, the position measurement unit 7640, the beacon reception unit 7650, the in-vehicle device I/F 7660, and the on-vehicle network I/F 7680, and may create local map information including nearby information at a current position of the vehicle. In addition, the microcomputer 7610 may predict danger such as collision of the vehicle, approaching of a pedestrian and the like, and entrance into a road for which traffic is closed on the basis of acquired information, and may generate an alarm signal. For example, the alarm signal may be a signal for generating an alarm sound or a signal for lighting an alarm lamp.

The sound and image output unit 7670 transmits an output signal of at least one of a sound or an image to an output device capable of notifying an occupant of a vehicle or an outer side of the vehicle of information in a visual manner or an auditory manner. In the example in FIG. 20, as the output device, an audio speaker 7710, a display unit 7720, and an instrument panel 7730 are exemplified. For example, the display unit 7720 may include at least one of an on-board display or a head-up display. The display unit 7720 may have an augmented reality (AR) display function. The output device may be other device such as a headphone, a wearable device such as an eyeglass-type display which the occupant wears, a projector, and a lamp in addition to the above-described devices. In a case where the output device is a display device, the display device visually displays results obtained through the various kinds of processing which are performed by the microcomputer 7610, or information received from other control units in various modes such as a text, an image, a table, and a graph. In addition, in a case where the output device is a sound output device, the sound output device converts an audio signal constituted by reproduced sound data, acoustic data, or the like into an analog signal, and outputs the analog signal in an auditory manner.

Furthermore, in the example illustrated in FIG. 20, at least two control units which are connected through the communication network 7010 may be integrated as one control unit. Alternatively, an individual control unit may be constituted by a plurality of control unit. In addition, the vehicle control system 7000 may include additional control units (not illustrated). In addition, in the description, a part or the entirety of a function of any one control unit may be provided in another control unit. That is, when transmission and reception of information through the communication network 7010 is established, predetermined operation processing may be performed by any one control unit. Similarly, a sensor or a device that is connected to any one control unit may be connected to another control unit, and a plurality of the control units may transmit and receive detection information to and from each other through the communication network 7010.

In the above-described vehicle control system 7000, the rear surface irradiation-type solid-state imaging element 50 to which the present technology is applied is applicable to the imaging unit 7410 illustrated in FIG. 20. When the rear surface irradiation-type solid-state imaging element 50 in FIG. 9 is applied to the imaging unit 7410, it is possible to obtain a more easily visible captured image, or it is possible to acquire distance information. In addition, it is possible to reduce fatigue of a drive or it is possible to enhance safety of the driver or a vehicle by using the captured image or the distance information which is obtained.

Furthermore, an embodiment of the present disclosure is not limited to the above-described embodiment, and various modifications can be made in a range not departing from the gist of the present disclosure.

The present technology may have the following configurations.

(1) A solid-state imaging element,
  in which each pixel includes
  a photoelectric conversion unit that performs photoelectric conversion in correspondence with incident light, and
  a microlens that condenses the incident light to the photoelectric conversion unit, and
  a pixel in which a multi-layered anti-reflective film is formed on a surface of the microlens and a pixel in which a single-layered anti-reflective film is formed on the surface of the microlens are mixed in.

(2) The solid-state imaging element according to (1),
  in which the pixel in which the single-layered anti-reflective film is formed on the surface of the microlens is a pixel obtained by removing an anti-reflective film having moisture permeability lower than moisture permeability of the single-layered anti-reflective film from the pixel in which the multi-layered anti-reflective film is formed on the surface of the microlens.

(3) The solid-state imaging element according to (1) or (2),
  in which at least pixels corresponding to one-fourth of the entirety of pixels are pixels in which the single-layered anti-reflective film is formed on the surface of the microlens.

(4) The solid-state imaging element according to any one of (1) to (3), further including:
  a color filter that is provided between the photoelectric conversion unit and the microlens, and
  in which all pixels, in which the color filter has a predetermined color, among the entirety of pixels are pixels in which the single-layered anti-reflective film is formed on the surface of the microlens.

(5) The solid-state imaging element according to (4),
  in which the color filter is formed in a Bayer array, and
  all pixels, in which the color filter is set to G, among the entirety of pixels are pixels in which the single-layered anti-reflective film is formed on the surface of the microlens.

(6) The solid-state imaging element according to (4),
  in which the color filter is formed in a Bayer array, and
  all pixels, in which the color filter is set to B, among the entirety of pixels are pixels in which the single-layered anti-reflective film is formed on the surface of the microlens.

(7) The solid-state imaging element according to (1),
  in which the multi-layered anti-reflective film is constituted by a first anti-reflective film and a second anti-reflective film,
  the single-layered anti-reflective film is constituted by the second anti-reflective film,
  the first anti-reflective film is a silicon nitride film or a silicon oxynitride film, and
  the second anti-reflective film is a silicon oxide film or a silicon oxycarbide film.

(8) The solid-state imaging element according to (7),
  in which refractive indexes of the microlens, the first anti-reflective film, and the second anti-reflective film satisfy a relationship of the first anti-reflective film>the microlens>the second anti-reflective film.

(9) The solid-state imaging element according to any one of (1) to (8),
  in which the solid-state imaging element is a rear surface irradiation type.

(10) A method for manufacturing a solid-state imaging element, including:
  forming a microlens that condenses incident light to a photoelectric conversion unit in each pixel; and
  forming a multi-layered anti-reflective film on a surface of the microlens in a first pixel, and forming a single-layered anti-reflective film on the surface of the microlens in a second pixel.

(11) An electronic device including:
  a solid-state imaging element,
  in which each pixel of the solid-state imaging element includes
  a photoelectric conversion unit that performs photoelectric conversion in correspondence with incident light, and
  a microlens that condenses the incident light to the photoelectric conversion unit, and a pixel in which a multi-layered anti-reflective film is formed on a surface of the microlens and a pixel in which a single-layered anti-reflective film is formed on the surface of the microlens are mixed in.

REFERENCE SIGNS LIST

50 Rear surface irradiation-type solid-state imaging element
PD Photodiode
51 Microlens
52 First anti-reflective film
53 Second anti-reflective film
54 Color filter
100 Imaging device
102 Solid-state imaging element

The invention claimed is:

1. A solid-state imaging element, comprising:
a plurality of pixels, wherein each of the plurality of pixels includes:
  a photoelectric conversion unit configured to perform photoelectric conversion in correspondence with incident light; and
  a microlens configured to condense the incident light to the photoelectric conversion unit, wherein
    a first pixel of the plurality of pixels has a multi-layered anti-reflective film on a surface of the microlens,
    a second pixel of the plurality of pixels has a single-layered anti-reflective film on the surface of the microlens,
    the second pixel is obtained based on removal of a first anti-reflective film of the multi-layered anti-reflective film from the first pixel, and
    a moisture permeability of the first anti-reflective film is lower than a moisture permeability of the single-layered anti-reflective film.

2. The solid-state imaging element according to claim 1, wherein at least one-fourth pixels of the plurality of pixels include the single-layered anti-reflective film on the surface of the microlens.

3. The solid-state imaging element according to claim 1, wherein
each of the plurality of pixels further includes a color filter between the photoelectric conversion unit and the microlens,
each of a set of pixels of the plurality of pixels has a specific color, and
each of the set of pixels includes the single-layered anti-reflective film on the surface of the microlens.

4. The solid-state imaging element according to claim 3, wherein
the color filter is in a Bayer array, and
each of the set of pixels is set to green (G).

5. The solid-state imaging element according to claim 3, wherein
the color filter is in a Bayer array, and
each of the set of pixels is set to blue (B).

6. The solid-state imaging element according to claim 1, wherein
the multi-layered anti-reflective film includes the first anti-reflective film and a second anti-reflective film,
the single-layered anti-reflective film includes the second anti-reflective film,
the first anti-reflective film is one of a silicon nitride film or a silicon oxynitride film, and
the second anti-reflective film is one of a silicon oxide film or a silicon oxycarbide film.

7. The solid-state imaging element according to claim 6, wherein
a first refractive index of the first anti-reflective film is higher than a second refractive index of the microlens, and
the second refractive index of the microlens is higher than a third refractive index of the second anti-reflective film.

8. The solid-state imaging element according to claim 1, wherein a type of the solid-state imaging element is a rear surface irradiation type.

9. A method for manufacturing a solid-state imaging element, the method comprising:
forming, in each of a plurality of pixels, a microlens that condenses incident light to a photoelectric conversion unit;
forming a multi-layered anti-reflective film on a surface of the microlens in a first pixel of the plurality of pixels; and
forming a single-layered anti-reflective film on the surface of the microlens in a second pixel of the plurality of pixels, wherein
the single-layered anti-reflective film is formed based on a removal of an anti-reflective film of the multi-layered anti-reflective film from the first pixel, and
a moisture permeability of the anti-reflective film is lower than a moisture permeability of the single-layered anti-reflective film.

10. An electronic device, comprising:
a solid-state imaging element comprises a plurality of pixels, wherein each of the plurality of pixels includes:
  a photoelectric conversion unit configured to perform photoelectric conversion in correspondence with incident light; and
  a microlens configured to condense the incident light to the photoelectric conversion unit, wherein
    a first pixel of the plurality of pixels has a multi-layered anti-reflective film on a surface of the microlens,
    a second pixel of the plurality of pixels has a single-layered anti-reflective film on the surface of the microlens,
    the second pixel is obtained based on removal of an anti-reflective film of the multi-layered anti-reflective film from the first pixel, and
    a moisture permeability of the anti-reflective film is lower than a moisture permeability of the single-layered anti-reflective film.

11. A solid-state imaging element, comprising:
a plurality of pixels, wherein each of the plurality of pixels includes:
  a photoelectric conversion unit configured to perform photoelectric conversion in correspondence with incident light; and
  a microlens configured to condense the incident light to the photoelectric conversion unit, wherein
    a first pixel of the plurality of pixels has a multi-layered anti-reflective film on a surface of the microlens,
    a second pixel of the plurality of pixels has a single-layered anti-reflective film on the surface of the microlens, and
    a type of the solid-state imaging element is a rear surface irradiation type.

* * * * *